United States Patent
Roberts et al.

(10) Patent No.: US 8,226,235 B2
(45) Date of Patent: Jul. 24, 2012

(54) METHOD AND APPARATUS FOR DETERMINING DYNAMIC DEFORMATION CHARACTERISTICS OF AN OBJECT

(75) Inventors: Cynthia J. Roberts, Columbus, OH (US); James Richard Marous, South Vienna, OH (US); Ashraf Mostafa Mahmoud, New Albany, OH (US)

(73) Assignee: Vision Optimization, LLC, Columbus, OH (US)

( * ) Notice: Subject to any disclaimer, the term of this patent is extended or adjusted under 35 U.S.C. 154(b) by 168 days.

(21) Appl. No.: 12/717,159

(22) Filed: Mar. 4, 2010

(65) Prior Publication Data

US 2010/0238408 A1 Sep. 23, 2010

Related U.S. Application Data

(63) Continuation-in-part of application No. 12/091,307, filed as application No. PCT/US2006/060381 on Oct. 31, 2006, which is a continuation-in-part of application No. 11/830,372, filed on Jul. 30, 2007, now Pat. No. 7,866,820, which is a continuation of application No. 11/674,985, filed on Feb. 14, 2007, now abandoned.

(60) Provisional application No. 60/731,756, filed on Oct. 31, 2005, provisional application No. 60/773,293, filed on Feb. 14, 2006.

(51) Int. Cl.
*A61B 3/10* (2006.01)
*A61B 3/16* (2006.01)
(52) U.S. Cl. ........... 351/212; 351/210; 600/405; 702/42
(58) Field of Classification Search .................. 351/205, 351/210, 211, 212, 221, 246, 247; 600/401, 600/405; 356/601, 610; 702/42, 50
See application file for complete search history.

(56) References Cited

U.S. PATENT DOCUMENTS

| | | | |
|---|---|---|---|
| 4,621,644 A | 11/1986 | Eilers | |
| 4,812,448 A | 3/1989 | Knepper | |
| 4,995,716 A * | 2/1991 | Warnicki et al. | 351/212 |
| 5,131,739 A | 7/1992 | Katsuragi | |
| 5,159,361 A | 10/1992 | Cambier et al. | |
| 6,042,544 A | 3/2000 | Miwa et al. | |
| 6,045,503 A | 4/2000 | Grabner et al. | |

(Continued)

OTHER PUBLICATIONS

Grabner et al.; Dynamic Corneal Imaging; J Cataract Refract Surg 2005; vol. 31: 163-174; 2005 ASCRS and ESCRS; Elsevier Inc.

(Continued)

*Primary Examiner* — Huy K Mai
(74) *Attorney, Agent, or Firm* — William Greener; Bond, Schoeneck & King, PLLC

(57) ABSTRACT

Apparatus and methods for measuring a dynamic deformation characteristic of a deformable target surface during a deformation interval. The measurement principles may be applied to a large variety of organic and inorganic materials having a surface that can be deformed by an applied non-contact force. The surface may be light diffusing and non-transparent or non-diffusing and transparent. A device for measuring a dynamic deformation characteristic of an in-vivo cornea during a deformation interval includes a corneal topographer and an air puff generator that are operationally integrated. Use of the inventive device enables a method for making a measurement of a deformation characteristic of the in-vivo cornea during a deformation interval, further allowing a determination of spatially-resolved in-vivo corneal biomechanical and biodynamic properties such as corneal elasticity and corneal viscosity.

34 Claims, 41 Drawing Sheets

U.S. PATENT DOCUMENTS

| | | | |
|---|---|---|---|
| 6,149,609 | A | 11/2000 | Lieberman et al. |
| 7,425,067 | B2 * | 9/2008 | Warden et al. ............... 351/205 |
| 7,871,378 | B1 * | 1/2011 | Chou et al. ................... 600/398 |
| 2006/0241367 | A1 | 10/2006 | Koest |
| 2007/0097317 | A1 | 5/2007 | Hsyashi et al. |
| 2008/0259276 | A1 | 10/2008 | Roberts |
| 2011/0118585 | A1 * | 5/2011 | Ishii et al. ................... 600/401 |

OTHER PUBLICATIONS

Edmund, C.; Corneal Topography and Elasticity in Normal and Keratoconic Eyes. A Methodological Study Concerning the Pathogenesis of Keratoconus; Acta Ophthalmol Suppl. 1989; vol. 193; Abstract.

* cited by examiner

METHOD AND APPARATUS FOR DETERMINING DYNAMIC DEFORMATION CHARACTERISTICS OF AN OBJECT

RELATED APPLICATION DATA

The instant application is a continuation-in-part of application Ser. No. 12/091,307 filed on Apr. 24, 2008, which is a 371 of International application Serial No. PCT/US2006/060381 filed on Oct. 31, 2006, which itself claims benefit of U.S. provisional application Ser. No. 60/731,756 filed on Oct. 31, 2005. The instant application is also a continuation-in-part of application Ser. No. 11/830,372 filed on Jul. 30, 2007, now U.S. Pat. No. 7,866,820 which is a continuation application of Ser. No. 11/674,985 filed on Feb. 14, 2007, now abandoned which itself claims priority to provisional application Ser. No. 60/773,293 filed on Feb. 14, 2006. The disclosures of all of the foregoing referenced applications are incorporated herein by reference in their entireties.

BACKGROUND OF THE INVENTION

1. Field of the Invention

Embodiments of the invention generally relate to methods and apparatus for measuring deformation characteristics of a deformable object through changes in, or displacement of, the surface of the object during, over, throughout, and simultaneous with (all hereinafter referred to as 'during") a deformation event or deformation time interval (referred to hereinafter as 'deformation interval') caused by an inflicted deformation or other perturbation (referred to hereinafter as 'deformation') of the surface, and determining elastic and/or viscoelastic properties of the object therefrom. More particularly, embodiments of the invention relate to apparatus and methods that provide the capability to determine biomechanical (non-time dependent) and biodynamic (time dependent), and other characteristics (e.g., intraocular pressure) of a live cornea through measured changes in the topographical characteristics, e.g., displacement of, the surface of the live cornea during a deformation interval caused by an inflicted deformation of the live corneal surface. Most particularly, embodiments of the invention pertain to apparatus and methods that provide the capability to obtain spatially-resolved measurements of displacement, stiffness, corneal elasticity, corneal viscosity, and other biomechanical and biodynamic properties across substantially the entire corneal surface or a more centralized region of a live cornea through changes in the surface topography of the cornea, and pressure measurements, during a deformation interval caused by an inflicted deformation of the live corneal surface.

2. Description of Related Art

The measurement of the surface characteristics or displacement of an object during, over, within, or throughout a deformation of the object's surface can reveal much information about the physical and mechanical properties of the object. If the surface of the object is deformable in response to an applied force, measurement of the changes in characteristics, as well as the amount of displacement of the surface may provide further useful information about the underlying structure of the object and an understanding of how the structure behaves.

There exists numerous organic and inorganic objects having deformable surfaces whose measurement may be of interest in various fields. A particularly interesting, exemplary object is the cornea of a living eye. The widespread interest in understanding the physical, biomechanical, biodynamic, optical, and all other characteristics of the eye is obviously motivated. Over the years, different theories have been presented about the biomechanical and biodynamic properties of the eye, particularly the cornea. Earlier, inaccurate models of the cornea as a solid, rigid structure have more recently given way to newer theories informing a more accurate understanding of the cornea as a layered, dynamic structure that to this day is not completely understood.

Measurement of the biomechanical (elastic) and biodynamic (viscous and viscoelastic) properties of the cornea have previously required a donor (dead) cornea that could be cut into strips and stretched to determine the stress/strain relationship needed to calculate elastic modulus; or an intact donor eye, where the intraocular pressure could be significantly raised in order to stretch the cornea and measure the stress/strain relationship. Alternatively, the viscoelastic properties could be measured by stretching dissected corneal strips and monitoring their changes over time. However, until the advent of the instant embodied invention, it was not known how to measure stress/strain relationships and viscoelastic properties of a live eye (i.e., in-vivo).

An increased but incomplete understanding of the structure of the cornea and its interaction with other components of the eye has been achieved indirectly by measuring various topographical characteristics of the cornea in an unperturbed or undeformed state. These topographical characteristics include corneal curvature and surface elevation with respect to a reference surface, as well as others known in the art. Devices for measuring various topographical characteristics of an object such as a cornea, for example, include topographers, keratographers and keratometers. As known in the art, a topographer is a generic term referring to an apparatus for measuring the topographical characteristics of an object surface. A keratometer is a device that measures corneal curvature only in the central 3 mm of the cornea by measuring the chord length of the virtual image of a target (e.g., ring patterns) imaged by the cornea, and determines curvature based on the index of refraction. A keratographer is a different device that is capable of making measurements beyond the central 3 mm region of the cornea based upon reflection from the anterior corneal surface rather than imaging through the cornea. Thus different devices use different measuring principles to determine various topographical characteristics of the cornea. For example, some devices use Placido-based reflective image analysis. Placido-based devices can measure curvature parameters of the cornea but typically lack the capability to directly measure surface elevation. The Orbscan® anterior segment analyzer (Bausch & Lomb Incorporated), on the other hand, is a topographical characteristic measuring device that utilizes a scanning optical slit. Device software provides for direct measurement of surface elevation and corneal thickness as well as surface curvature. Another commercial device developed by Par Technology Corporation is known as the PAR CTS™ Corneal Topography System (PAR). The PAR CTS system utilizes a raster photography method. The PAR CTS operates by projecting a known grid image onto the anterior corneal surface that is viewed by a camera from an offset axis. Other topographical characteristic measuring techniques may include Scheimpflug Tomography, confocal microscopy, optical coherence tomography, ultrasound, optical interferometry, and others, all of which are well known in the art.

While the measurement of various topographical characteristics of the cornea provide a wealth of information about vision and the effects of corneal shape on visual performance, corneal topography by itself cannot reveal the biodynamic and biomechanical properties of the cornea necessary for a thorough understanding of its structure and functional operation; thus it is necessary to know something about the elastic and viscoelastic properties of the cornea. For example, Liu and Roberts, *J Cataract Refract Surg* 2005; 31:146-155, first recognized the impact that biomechanical and biodynamic properties of the cornea have on intraocular pressure (IOP).

An illustrative apparatus in which biomechanical properties have been determined to influence the measurement process, unknown to the user and responsible for errors in measurement, is a tonometer. Tonometers, which are devices for determining intraocular pressure (IOP), were originally developed as contact-type instruments, meaning that a portion of the instrument is brought into contact with the corneal surface during the IOP measurement procedure. A well known instrument of this type is the Goldmann applanation tonometer (GAT), originally developed in the 1950s. The GAT measures the force required to flatten ("applanate") a known area of the cornea, from which IOP can be determined if assumptions are made about the thickness and properties of the cornea. The GAT is used today as a standard against which other types of tonometers are compared to assess measurement accuracy.

It has been reported in the literature that corneal thickness generates errors in GAT measurements. However, it has also been theoretically predicted that biomechanical properties (e.g., elastic modulus) have a greater influence on measurement error than corneal thickness. Id.

Patient discomfort caused by contact tonometers such as the GAT led to the development of "non-contact" tonometers, which operate by directing an air pulse generated by a pump mechanism through a discharge tube aimed at the cornea to cause applanation. As the cornea is deformed by the fluid pulse, an optoelectronic system monitors the cornea by detecting corneally-reflected light from a beam obliquely incident upon the cornea. A peak detector signal occurs at the moment of applanation when the reflecting surface of the cornea is flat. During a non-contact IOP measurement, and depending on the characteristics of the piston, the cornea is actually deformed from its original convex state through a first state of applanation to a slightly concave state and then through a second state of applanation to convexity as the air pulse decays.

A method for measuring air puff force and determining IOP, and a non-contact tonometer, are disclosed in U.S. Pat. Nos. 6,419,631 and 6,875,175, the disclosures of which are hereby incorporated by reference in their entireties to the fullest extent allowed by applicable laws and rules. This technology is commercially known as the Reichert (Depew, N.Y.) Ocular Response Analyzer™. According to posted information accessible at http://ocularresponse.reichertoi.com, the Reichert Ocular Response Analyzer utilizes a dynamic bidirectional applanation process to measure a cornea tissue property called corneal hysteresis. The term corneal hysteresis refers to the difference in pressure values of the air pulse at the inward moving applanation point and the outward moving applanation point during a measurement interval (inward moving refers to an initial convex corneal shape moving to a flattened condition, while the outward applanation point refers to the maximum air pulse concave corneal surface moving towards the applanation point on its return to a normal convex surface shape as the air pressure decays). Since corneal hysteresis appears to be a repeatable measurement, it may provide a metric that is useful for identifying and categorizing various conditions of the cornea. For example, measurement of corneal hysteresis is alleged to aid in identifying and classifying conditions such as corneal ectasia and Fuch's Dystrophy, and as helping in the diagnosis and management of glaucoma. Differences in hysteresis measurements for different corneal conditions may better inform about the biomechanical and biodynamic properties of the cornea. Because corneal hysteresis measurement is credited for presenting one characterization of the cornea's biomechanical state, it is believed to have additional potential uses in screening refractive surgery candidates as well as predicting and controlling surgical outcomes. However, none of these predictions and controlling of surgical outcomes have been validated in scientific studies. In addition, corneal hysteresis is not a measurement of elastic modulus or corneal stiffness. It has been reported in the literature that hysteresis does not correlate to elastic modulus by its very nature. The same value of hysteresis is associated with multiple combinations of viscosity and elasticity. For example, low hysteresis is associated with both a soft cornea in the case of keratoconus, and a stiff cornea in the case of an older eye or an eye with higher pressure. Hysteresis has been shown to decrease with a subject's age, where it is well known in the art that corneas stiffen with age. Therefore, corneal hysteresis is not the answer to providing a quantitative measurement of corneal biomechanical and/or biodynamic properties.

There is thus a clear need to be able to measure corneal biomechanical and biodynamic properties in-vivo, which to the inventor's knowledge has never been accomplished on a live eye.

In view of the shortcomings of the above described techniques, capabilities, and apparatus for measuring corneal topographical characteristics, hysteresis, and other known parameters in a serial manner, the inventor has recognized that additional benefits could be obtained by developing an apparatus and method that involve integration of the different concepts and are capable of real-time, in-vivo measurements of corneal biomechanical properties. The inventor has further recognized the need for new and improved methods and apparatus that are capable of measuring and quantifying biomechanical properties of the cornea in a manner not previously demonstrated or accomplished, such as making and obtaining spatially-resolved, in-vivo corneal deformation characteristic measurements over a specified region of the cornea (e.g., central cornea or corneal-scleral region), resulting in a better understanding of corneal biomechanics and biodynamics.

These and other advantages and benefits are achieved by the invention, which will be described in detail below and with reference to the drawings.

SUMMARY OF THE INVENTION

Embodiments of the invention are generally directed to apparatus and methods for measuring a selected topographical characteristic of a deformable object surface both before and during a deformation interval over which the object surface is deformed via the apparatus, and using the measurement information and other measured or supplied information (e.g., IOP) to determine elastic and viscoelastic characteristics and properties of the object. It is to be understood that the measurement principles of the invention may be applied to a variety of organic and inorganic materials having a surface that can be deformed by an applied non-contact force or other perturbation. The surface may be light diffusing and non-transparent or non-diffusing and transparent.

The exemplary and illustrative embodiments of the invention will be disclosed herein below in the non-limiting context of making in-vivo, spatially-resolved measurements over a selected region of a (live) cornea both before and during a deformation interval provided by the embodied device and over which the corneal surface is undergoing deformation, and using these measurements and other appropriate information (determined in-vivo or supplied) to quantitatively and qualitatively determine biomechanical and biodynamic properties and characteristics of the live cornea. In various aspects, the surface region of the cornea being characterized may vary from about a 5 mm or less diameter region about the center of the cornea to substantially the entire corneal-scleral region. The size of the corneal region being characterized may be limited by the operable distance of the corneal surface from the apparatus. For example, if an air puff mechanism is used to deform the cornea, the par-focal separation between the cornea and the apparatus may constrain the characterizable region of the cornea to less than substantially the entire corneal-scleral region.

An embodiment of the invention is directed to a device that enables making in-vivo measurements of selected topographical characteristics of a cornea both before and during a temporal period of corneal deformation provided via the device, and from which can be determined biomechanical and biodynamic properties of the (live) cornea. The device comprises the novel 'operational integration' of a topographer component and a non-contact surface deformer component. According to an aspect, the non-contact surface deformer component is located along a first, central, operational axis of the device. According to an aspect, the non-contact surface deformer component is an air pressure pulse-based apparatus (e.g., tonometer). In a particular aspect, the non-contact surface deformer component can deliver a calibrated air puff.

The topographer component includes a camera, which may, but need not be a high speed camera, disposed along a second, operational axis of the device that is directionally independent from the first, central axis; i.e., the axes are non-parallel and non-collinear, and may be non-coplanar. The topographer component further includes an optical system that includes a grid object and a light source for projecting a grid image onto the cornea, disposed along a third, operational axis of the device that is directionally independent from the first and second axes. In an exemplary aspect in which the object is a live eye, the topographer component is a computer-assisted, videokeratography-based topographer, and such a device as disclosed herein will be referred to as a dynamic Rasterstereographic Corneal Topographer ("d.RCT").

Exemplary selected topographical characteristics measurable by the embodied device may include, but are not limited to, surface displacement, surface curvature, surface elevation, surface indentation, surface deformation symmetry, surface deformation shape, and surface deformation area, all of which may be obtained in-vivo before and during a deformation interval, and which measurements further facilitate the quantitative determination of elastic and viscoelastic properties of a live eye.

As used throughout this specification and in the claims appended hereto, the phrase 'operationally integrated' is defined to mean that the deformation force-providing component and the topographer component both are physically integrated and co-operate simultaneously over a deformation event time interval and share optical measurement pathways in order to make biomechanical and/or biodynamic measurements of the cornea. In other words, each component is dependent upon the other and neither can stand alone for operational functionality (i.e., measuring biodynamic and biomechanical characteristics of a live cornea before and during corneal deformation over a deformation time interval according to the embodiments of the invention.

An embodiment of the invention is directed to a method for determining biomechanical (i.e., elastic) and biodynamic (i.e., viscoelastic) properties of a live eye that heretofore have not been possible to measure or determine as such. According to a general, illustrative, non-limiting aspect, the method involves the steps of obtaining at least only a single in-vivo measurement image of a selected topographical characteristic of a cornea in an undeformed state; deforming the cornea with a known amount of a non-contact force applied during a deformation interval; obtaining at least only a single in-vivo measurement image of the selected topographical characteristic of the cornea in a deformed state being due to the known amount of the non-contact force applied during the deformation interval; determining a difference between the measured pre- and intra-deformation topographical characteristic values of the cornea at least only a single spatial location on the cornea, and deriving biomechanical and/or biodynamic measurements using this measured data and other appropriate measured or supplied data (e.g., IOP). In an aspect, the method may further comprise obtaining a plurality of in-vivo, topographical characteristic measurement images of the cornea in the deformed state during the deformation interval. In an aspect, the method may further comprise determining a displacement of the live cornea between the undeformed state and the deformed state at least two spatially-resolved locations on the cornea during the deformation interval. In various non-limiting aspects, the method further involves the determination of a measure of one or more of the stiffness, strain, elasticity, viscosity, and viscoelasticity of the live cornea, which measurements, according to the embodied invention, can provide a quantitative determination of the biomechanical and biodynamic properties of the live cornea.

Additional features and advantages of the invention will be set forth in the detailed description which follows, and in part will be readily apparent to those skilled in the art from that description or recognized by practicing the invention as described herein, including the claims as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DETAILED DESCRIPTION OF EMBODIMENTS OF THE INVENTION

Figure 1:
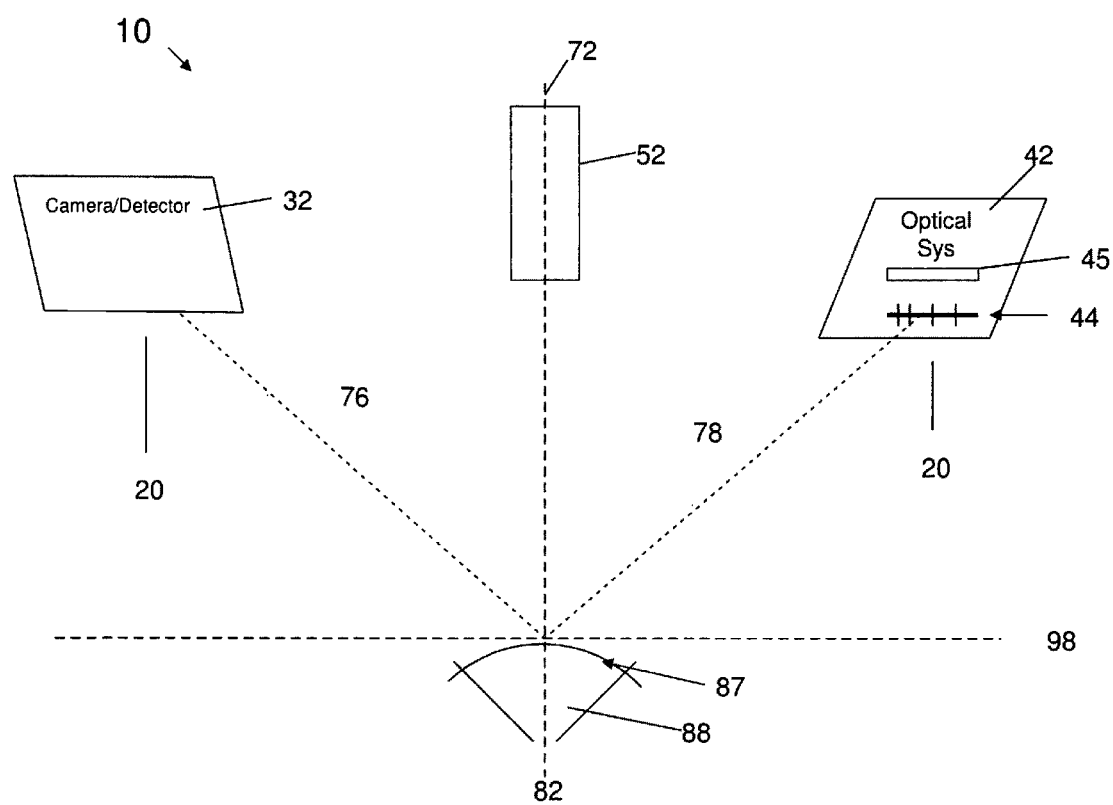
FIG. 1 is a schematic plan view of a device according to an embodiment of the invention.

As shown schematically in FIG. 1, an exemplary embodiment of the invention, referred to as the d.RCT, is a device 10 that enables making topographical deformation characteristic measurements of an in-vivo cornea 87 (of a live eye 88) before and during a deformation interval, and which, therefrom, enables the quantitative determination of biomechanical and biodynamic properties of the in-vivo cornea, that were heretofore unobtainable/indeterminable. The device 10 includes a topographer component 20 and a non-contact surface deformer component 52, that are 'operationally integrated' as that term is defined above.

The non-contact surface deformer component 52, which may be a calibrated air-puff generator or tonometer, is disposed along a first operational axis 72 of the device. The topographer component 20 includes an optical system comprising a camera/detector 32 disposed along a directionally-independent (as that term is defined above) second operational axis 76 of the device and a grid projection assembly 42 including an object grid 44 and a light source 45 for projecting a grid image onto the in-vivo cornea, disposed along a directionally-independent third operational axis 78 of the device. The camera 32 can capture a single image of the in-vivo corneal surface with the grid image overlayed thereon upon a selected triggering event, or multiple images according to an aspect where the camera/detector may be a high-speed camera. Various lenses and filters that are components of the topographer 20 are not shown. The live eye 88 is located along axis 82, which may be the same as device operational axis 72, in a measurement plane (projecting out of the paper) illustrated by dotted line 98.

Figure 4:
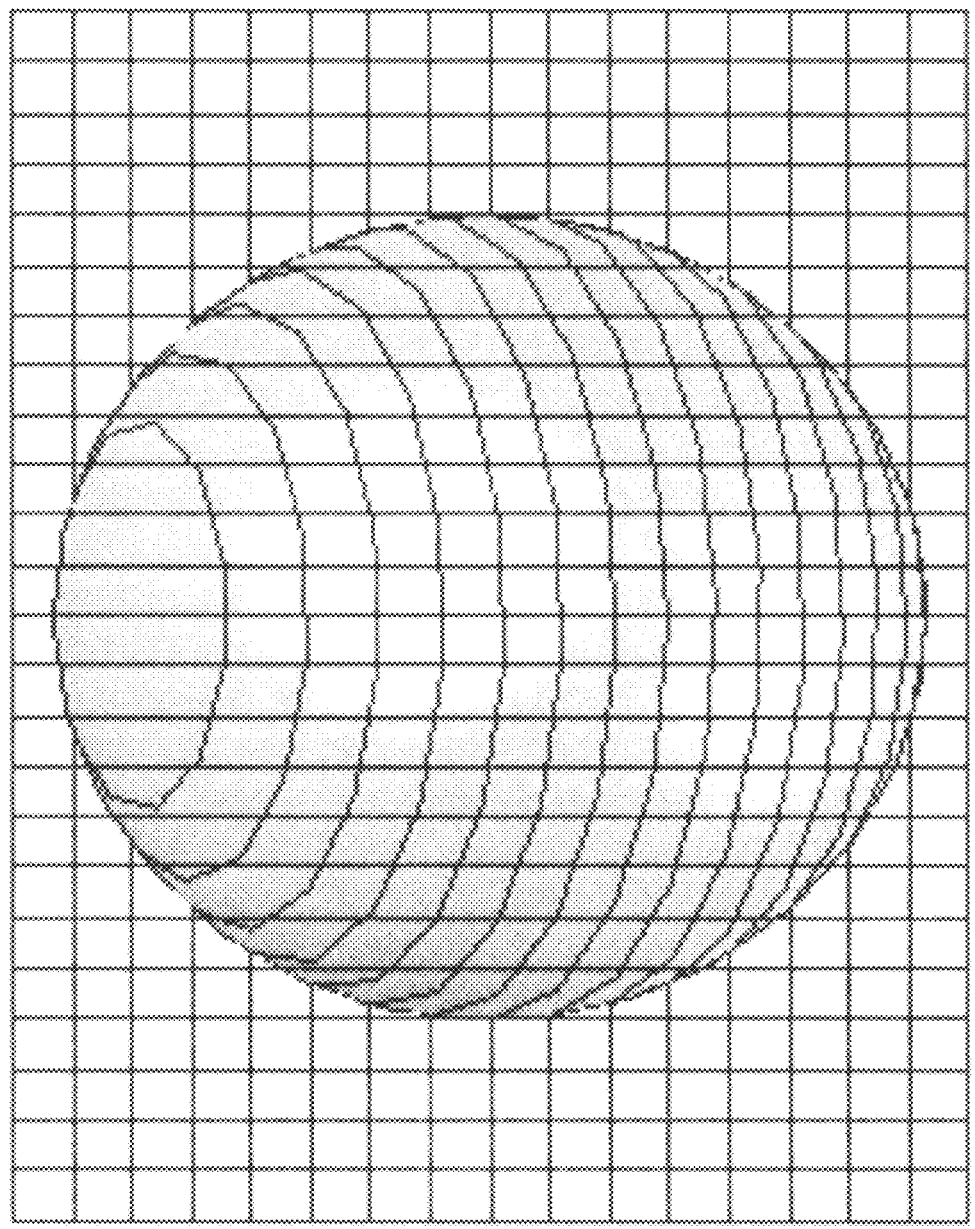
FIG. 4 is a top view of a projected d.RCT grid on a simulated cornea before air puff deformation of the corneal surface.

Once the cornea is suitably positioned in the measurement plane 98, measurement begins, according to an aspect, with the acquisition of an image of the in-vivo cornea/grid in an undeformed state, as illustrated in FIG. 4.

Figure 2A:
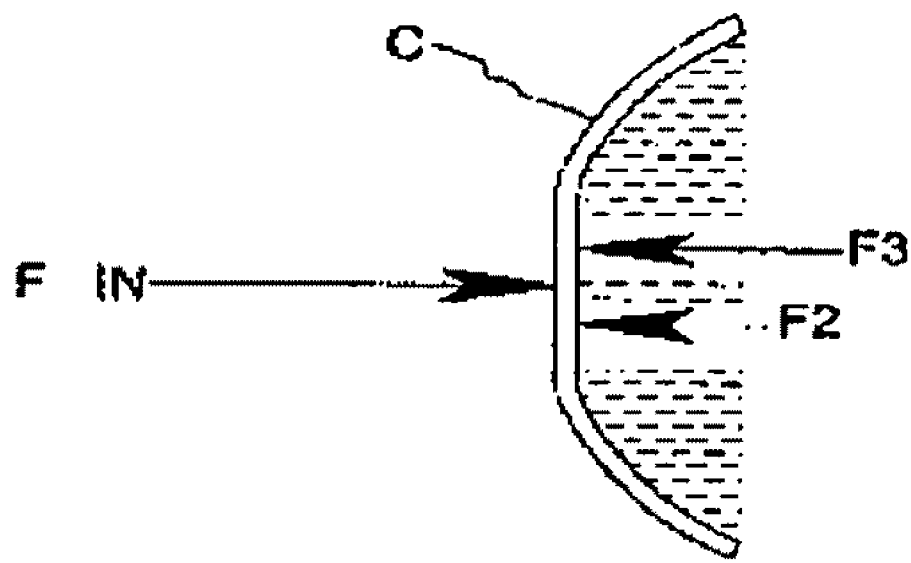
FIG. 2A is a schematic force diagram of a cornea at a first moment of applanation.
Figure 2B:
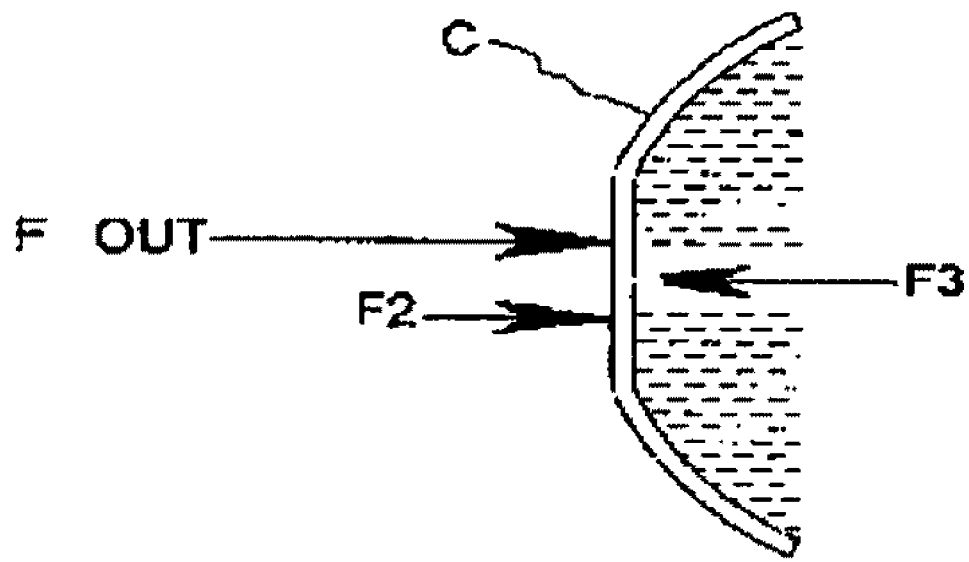
FIG. 2B is a schematic force diagram of a cornea at a second moment of applanation.
Figure 3:
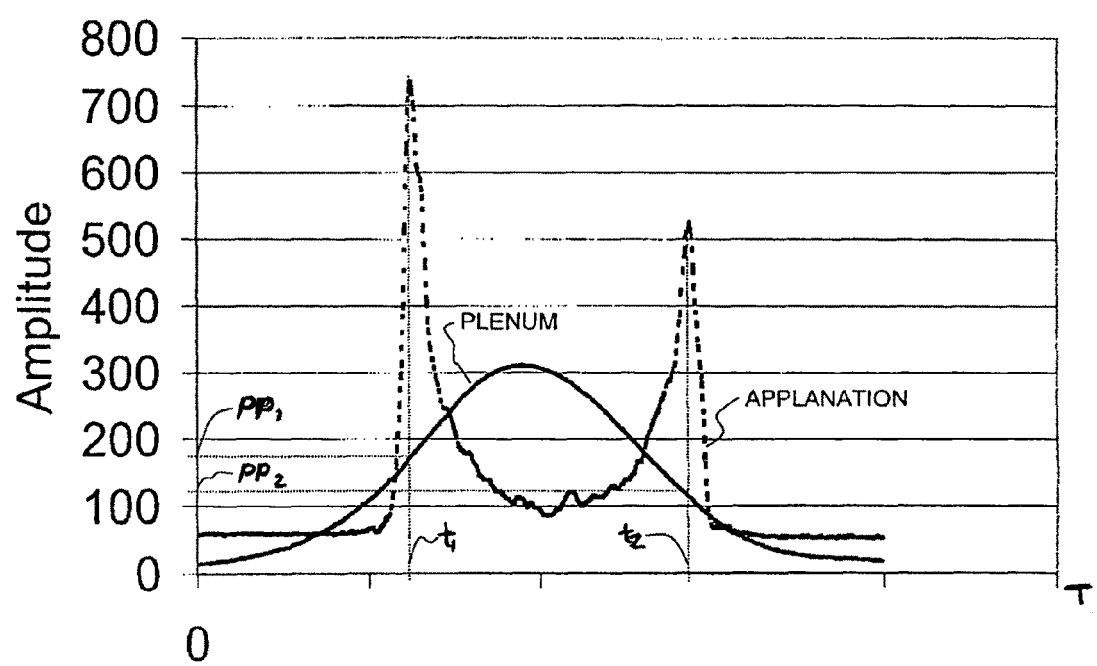
FIG. 3 is a graph showing applanation detection and plenum pressure signals for a deformation characteristic measurement according to an embodiment of the invention.

A metered air pulse is then generated and directed at the in-vivo cornea. The impulse energy imparted to the cornea by the air pulse reversibly deforms the cornea from its original state of convexity through a first state of applanation, $P_1$, to a state of concavity. As the air pulse decays or is controllably diminished, the in-vivo cornea returns from concavity back through a second state of applanation, $P_2$, to its original state of convexity. This deformation occurs over a deformation interval T as referenced in FIG. 3. FIGS. 2A and 2B are simplified diagrams showing the forces acting on a cornea C at the moment ($t_1$) of first applanation (FIG. 2A) and second ($t_2$) applanation (FIG. 2B) during the measurement interval, while ignoring dynamic effects. In the figures, $F_1$ represents the inwardly directed force of an incident air pulse, $F_2$ represents the force required to bend the corneal tissue itself, and $F_3$ represents the outwardly directed force attributed to intraocular pressure.

The topographer component 20 can conveniently be triggered off of event $P_1$ at time $t_1$, event $P_2$ at time $t_2$, at peak plenum pressure, and/or at any predetermined trigger point(s) over the deformation interval T to obtain a single, or a series of, intra-deformation images of the deformed in-vivo cornea/grid that facilitate an in-vivo corneal deformation characteristic measurement. It is advantageous to employ an air-puff generating, non-contact surface deformer component 52 that provides a measurable, if not consistent, air puff, with detection of the peak air pressure if timing is not consistent, or with consistent timing, in order to trigger the topographer prior to deformation and at least one deformation point during the deformation interval T.

The d.RCT Device

Figure 8:
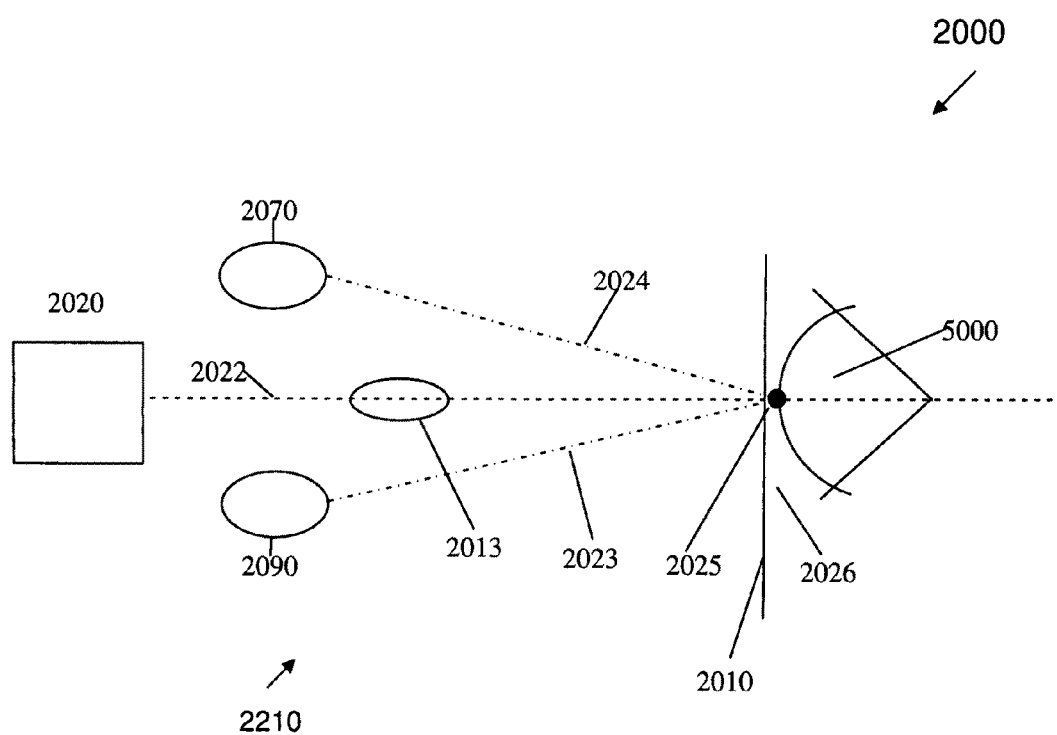
FIG. 8 is a schematic view of the d.RCT device according to an embodiment of the invention.
Figure 9:
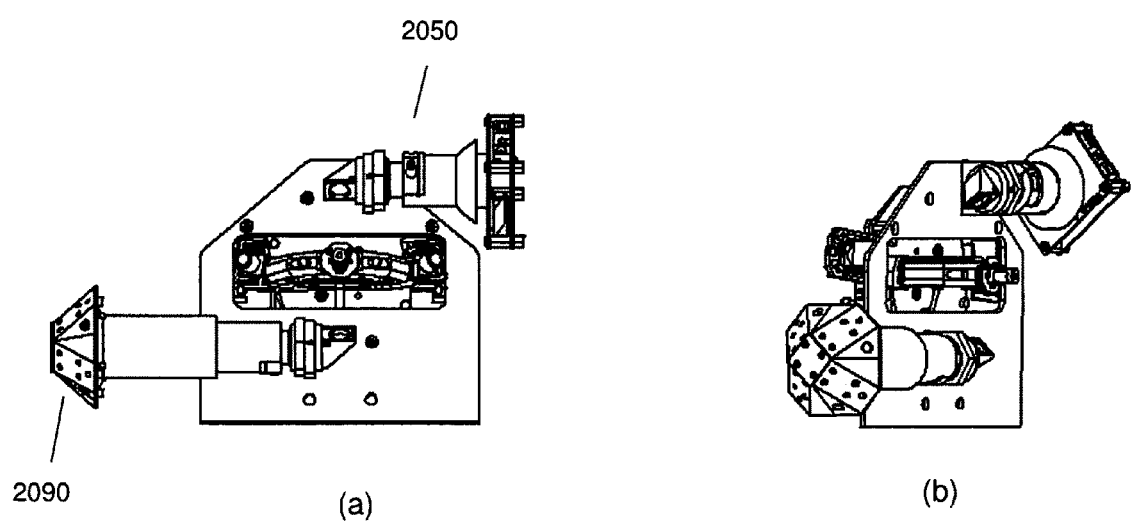
FIGS. 9a, 9b are schematic views of the d.RCT device according to an illustrative aspect of the invention.

According to a non-limiting, illustrative aspect, the d.RCT 2000 is shown in a side schematic view in FIG. 8. The d.RCT 2000 includes an optical head 2210 that is coupled to a controller/processor component(s) 2020. The optical head 2210 includes a camera assembly 2090 (that is to be) aligned with a target 5000 along axis 2023, and a grid projector assembly 2070 also (to be) aligned with the target 5000 along directionally independent axis 2024. FIG. 8 further shows the alignment of the camera system 2090 and the grid projector system 2070 in relation to the air puff nozzle 2013 aligned along directionally independent axis 2022. Axis 2022 is a vector along which the jet of compressed air travels towards the target 5000. Camera optical axis 2023 and projector optical axis 2024 are configured to present a focal point 2025 at the apex of the cornea, the same point at which the (Gaussian-distributed) air puff is designed to impinge upon the cornea.

Optomechanical Layout of the d.RCT

Figure 10:
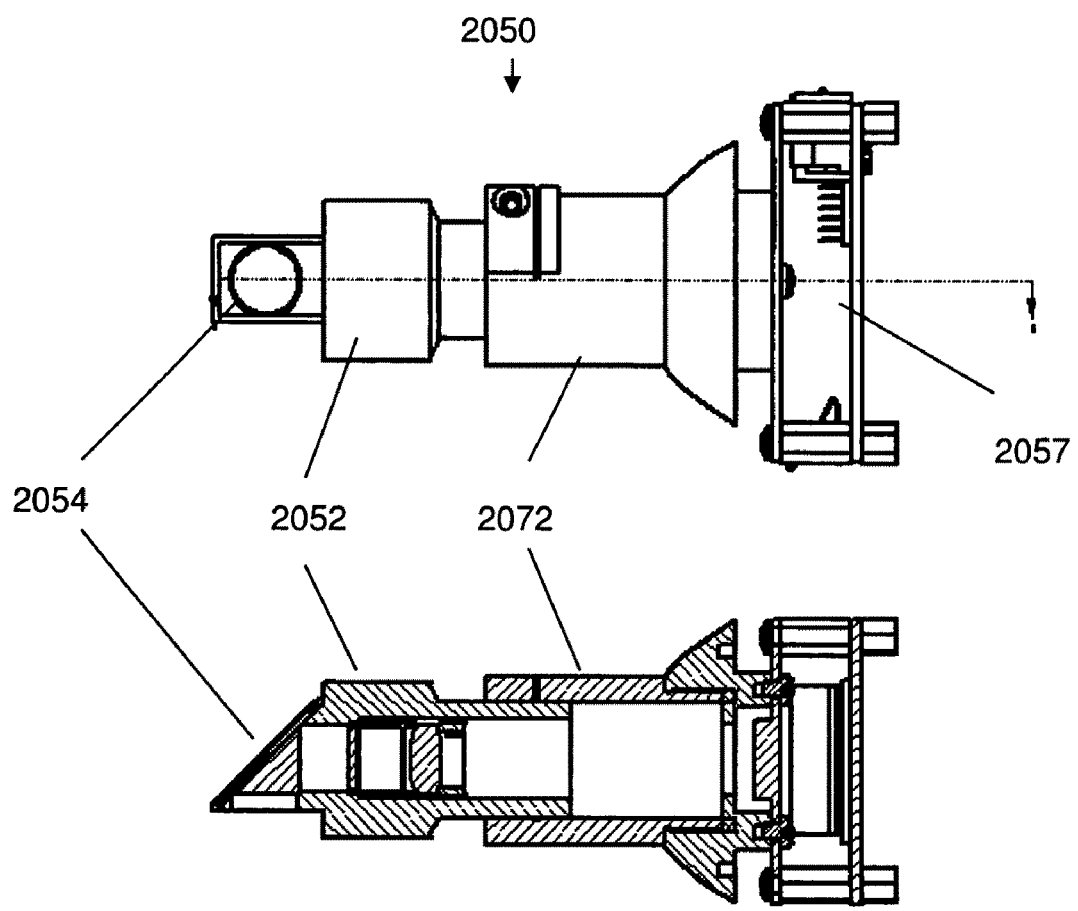
FIG. 10 is a schematic view of the camera assembly of the d.RCT device according to an illustrative aspect of the invention.
Figure 11:
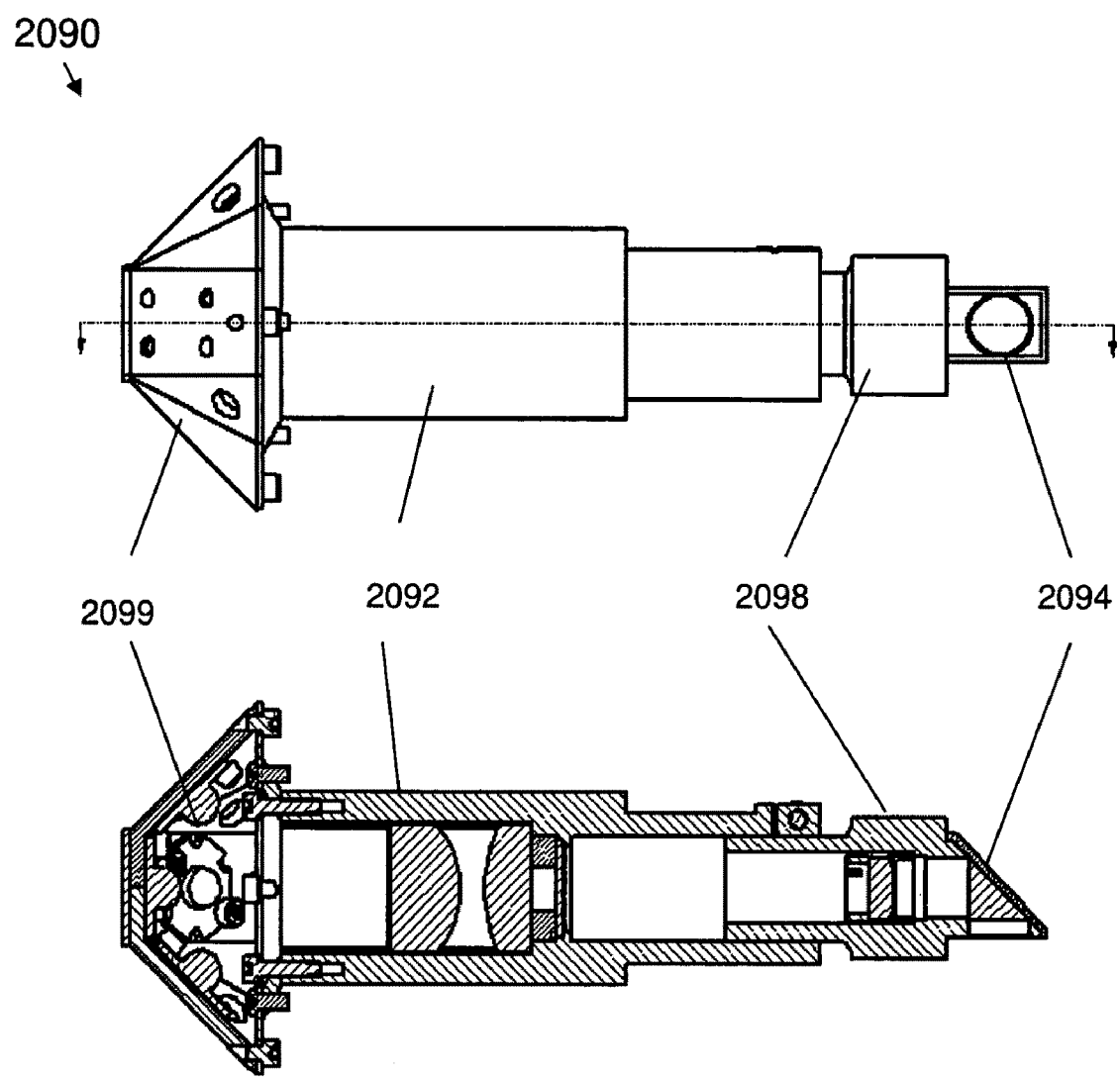
FIG. 11 is a schematic view of the projection assembly of the d.RCT device according to an illustrative aspect of the invention.

Referring to FIGS. 9a, 9b, 10 and 11, the optical assemblies of the grid camera assembly 2050 as illustrated in FIG. 10 includes an imaging optics enclosure 2052, 2072, prism 2054, and camera 2057. Similarly, the grid projector 2090 as illustrated in FIG. 11 includes a grid projection optics enclosure 2092 and 2098, prism 2094, and LED assembly 2099. The prisms provide optical path steering between the target, the cameras, and the grid projector. The optics enclosures 2052, 2072, 2092 and 2098 house optical assemblies and, as shown, are in the form of tubes. Adjustment of the relative positioning of camera optics enclosures 2052 and 2072, as well as adjustment of projector optics 2092 and 2098, allow for focusing adjustment of the optical assemblies.

Optical/Camera Hardware System

The d.RCT advantageously has a relatively short overall layout (compared, e.g., to the PAR CTS), as well as the capability to measure and analyze the topography of the in-vivo cornea, limbus and neighboring scleral region. A telephoto optical system in conjunction with limiting apertures also provide a generous depth of field (DoF), which in an aspect equals or exceeds 5 mm, whereas conventional corneal topography systems typically are limited to a DoF of less than 3 mm. The larger depth of field is advantageously used to image both the in-vivo cornea before deformation and during deformation with an air puff, without which the image may otherwise be out of focus and therefore inadequate for determining the biomechanical and biodynamic properties of the in-vivo cornea. The capability to map the in-vivo cornea, limbus, and neighboring sclera provides otherwise unavailable data that can also be useful for applications such as, but not limited to, fitting contact lenses and/or in intra-operative procedures.

A controllable, multi-wavelength, variable intensity LED (2099) illumination system according to an aspect of the invention provides instrumentation capability not associated with earlier generation corneal topography systems. For example, the combination of a cyan grid and fluorescein dye may not be optimum under all contemplated conditions of use of the d.RCT. It may be desirable to illuminate the target surface with IR light, in which case the use of a fluorescent substance such as Indocyanine Green (ICG) in place of fluorescein dye may be advantageous. Thus the capability for selecting an appropriate illumination wavelength can be provided by the LED illumination system of the d.RCT. The controllable LED illumination system allows a particular fluorescent compound to be targeted by an appropriate corresponding illumination wavelength.

System Electronics

Flash Controller Electronics

Figure 12:
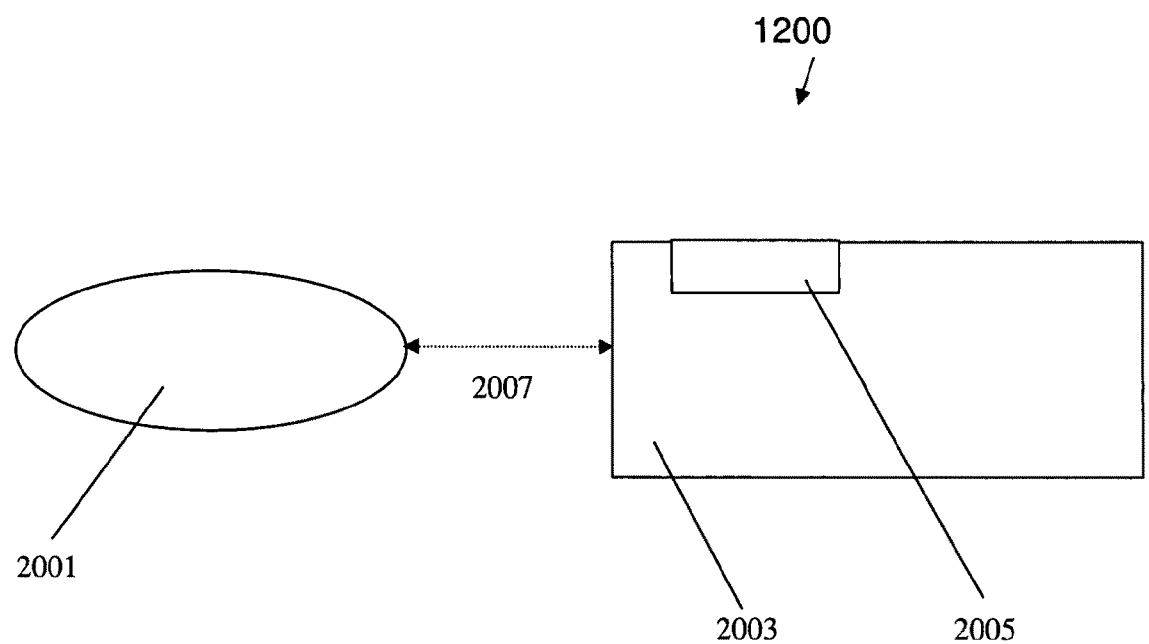
FIG. 12 is a block diagram of a flash controller assembly of the d.RCT device according to an illustrative aspect of the invention.

A flash controller assembly 1200 is shown schematically in FIG. 12. The flash controller components perform functions related to the grid illumination and digital input/output processing of the system. More specifically, the flash controller components turn the LED(s) 2099 on and off, provide LED illumination at multiple intensities at a specific light wavelength, and processes digital input/output for switches, indicator lights, etc.

In further detail, a flash controller 2003 is designed to accomplish two primary tasks. Firstly, the flash controller utilizes an available Universal Serial Bus (USB) port on a PC 2001 of the d.RCT 2000 to pass data to and from the host PC 2001 to the flash controller 2003. Secondly, this interface is designed to provide fast communications and be easy to interface with by a programmer.

Figure 13:
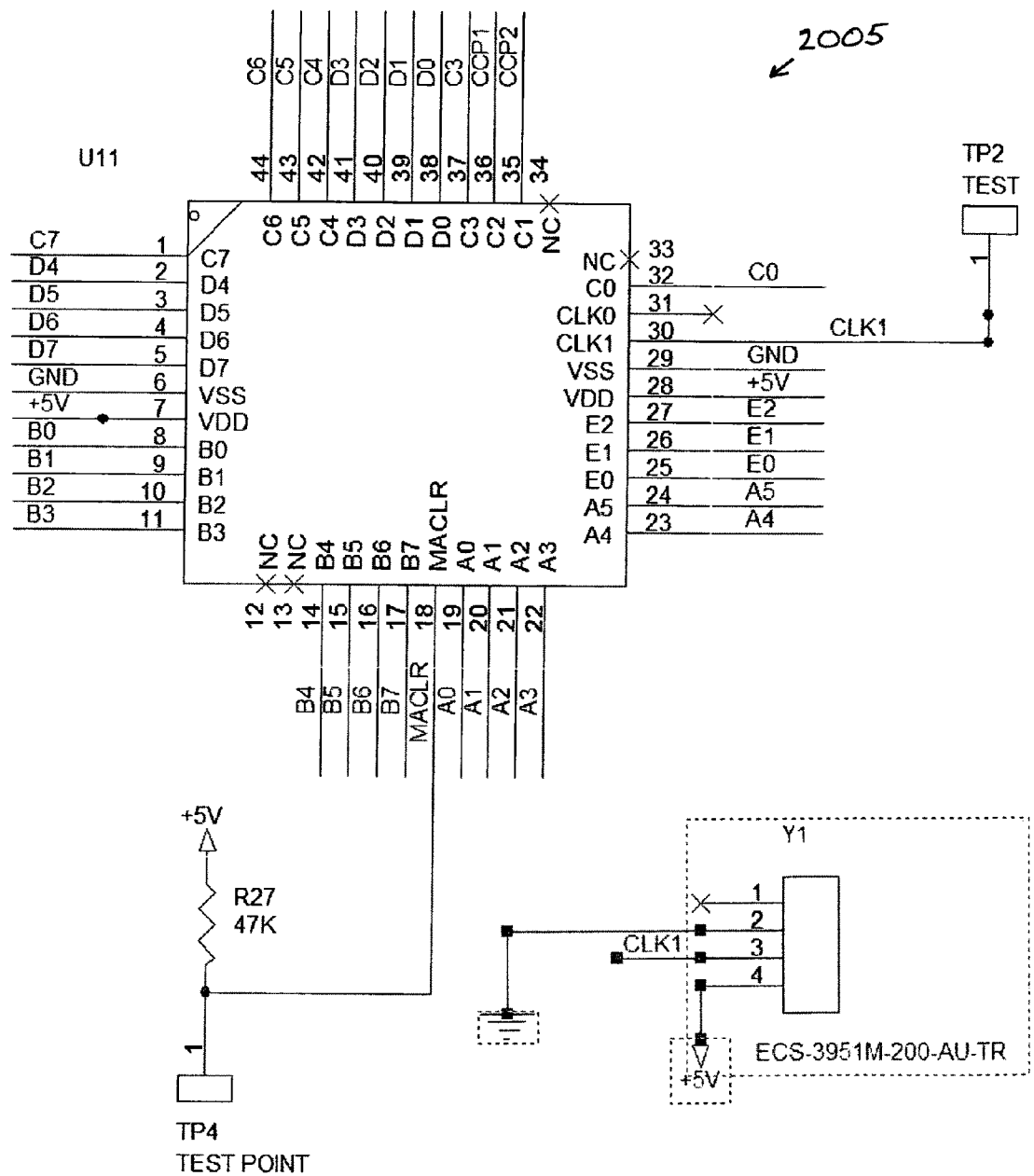
FIG. 13 shows a reset circuit of the d.RCT device according to an illustrative aspect of the invention.

According to an exemplary implementation, the flash controller 2003 utilizes a microprocessor based Peripheral Interface Controller (PIC) 2005. The PIC 2005 is driven by a 20 MHz crystal oscillator and reset circuit, as shown in FIG. 13. The PIC is software configured (with software authored in ANSI standard C programming language) to wait for commands from the PC 2001, execute these commands when properly received, and send data to the PC, as illustrated by arrow 2007 in FIG. 12.

Figure 14:
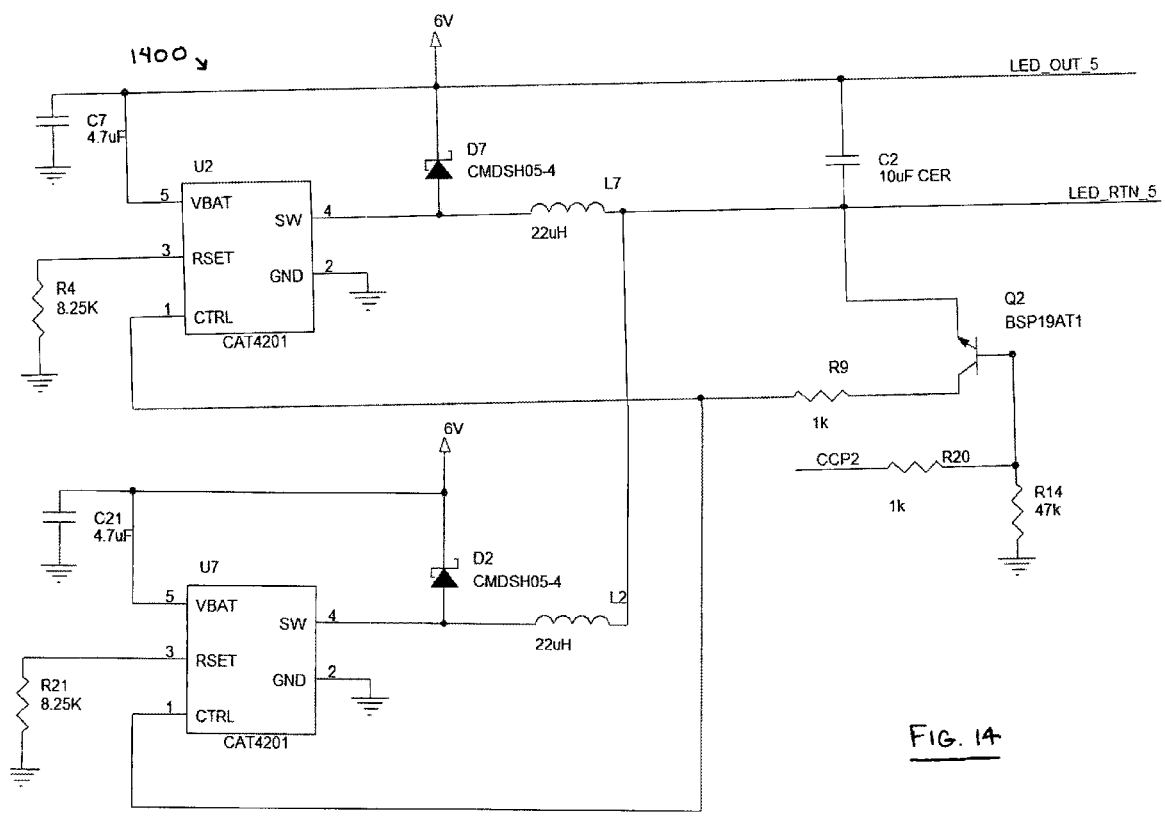
FIG. 14 shows a LED driver circuit of the d.RCT device according to an illustrative aspect of the invention.

According to an exemplary implementation, the flash controller 2003 utilizes five identical 700 milliamp driver circuits to illuminate five individual LEDs as illustratively shown by one driver circuit 1400 in FIG. 14.

According to an exemplary implementation, the flash controller 2003 utilizes Pulse Width Modulation (PWM) technology to adjust the light intensity of the LEDs. According to an exemplary implementation, the flash controller 2003 utilizes multiple PWM channels to independently drive multiple banks of LEDs having differing output wavelengths. By altering the relative intensity of each bank, the major illumination wavelength band of the light output by the LEDs can be controlled.

According to an exemplary implementation, the flash controller 2003 utilizes 2048 bits of electrically erasable programmable read-only memory (EEPROM) for non-volatile storage of data, which is retained with or without power applied to the flash controller.

According to an aspect, the interface utilizes only two 8-bit command bytes to instruct the PIC. The two bytes are formatted as follows:

first 8 bits—Flash controller command byte;
second 8 bits—Data byte;

The first byte is the flash controller command byte. This byte holds the command that the flash controller will immediately execute. The second byte is the data as further described below. The valid commands that may be issued are:

cmd_flashon: Turn both PWMs on for set duration
    cmd_flashoff: Turn both PWMs off
    cmd_torchon: Turn both PWMs on continuous
    cmd_torchoff: Turn both PWMs off
    cmd_flashon1: Turn only PWM CCP1 on for set duration
    cmd_torchon1: Turn only PWM CCP1 on continuous
    cmd_flashoff1: Turn only PWM CCP1 off
    cmd_torchoff1: Turn only PWM CCP1 off
    cmd_flashon2: Turn only PWM CCP2 on for set duration
    cmd_torchon2: Turn only PWM CCP2 on continuous
    cmd_flashoff2: Turn only PWM CCP2 off
    cmd_torchoff2: Turn only PWM CCP2 off
    cmd_setdutycycle1: Set the duty cycle of PWM CCP1 (int data1)
    cmd_getdutycycle1: Returns the duty cycle of PWM CCP1 (int)
    cmd_setdutycycle2: Set the duty cycle of PWM CCP2 (int data1)
    cmd_getdutycycle2: Returns the duty cycle of PWM CCP2 (int)
    cmd_reset: Resets board
    cmd_LEDson: Turn on user LEDs based on data1 (data1=LED #)
    cmd_LEDsoff: Turn user LEDs off based on data1 (data1=LED #)
    cmd_getLEDstatus: Returns current LED status (int)
    cmd_testboard: Runs built-in self test of board, returns result (int)
    cmd_readcal: Reads calibration data from eeprom into PIC memory
    cmd_writecal: Writes calibration data form PIC memory to eeprom
    cmd_getver: Returns PIC firmware version number (int)
    cmd_clearportb: Clears values saved in portb (sets to 0xff)
    cmd_getportb: Returns values in port b(int)
    cmd_writeportb: Writes value of data1 to port b (int)
    cmd_getportd: Returns values in port d (int)
    cmd_writeportd: Writes value of data1 to port d (int)
    cmd_setflashdur: Sets flash duration in milliseconds (data1)
    cmd_getflashdur: Returns flash duration in milliseconds (int)
    cmd_setver: Sets firmware version number
    cmd_gen_checksum: Generate firmware checksum According to another aspect, in addition to the host PC 2001 sending data to the flash controller 2003, the flash controller can also send data to the host PC. This may also be accomplished by utilizing a USB interface According to an aspect, the flash controller also can execute a test mode function so that the host PC can verify proper operation of the flash controller. Upon entering the test mode, the PIC will execute specific software commands to test the internal Rapid Access Memory (RAM), internal Read Only Memory (ROM), external EEPROM, and board mounted indicator LEDs. Results of the self test can then be displayed on the board mounted indicator LEDs and reported back to the host PC through the USB port.

According to an aspect, the flash controller also contains a reset mode so that the host PC can return the flash controller to a known state. When a reset is issued, the PIC returns to the powered on state and all default memory values are loaded from EEPROM.

Data Collection

Figure 5:
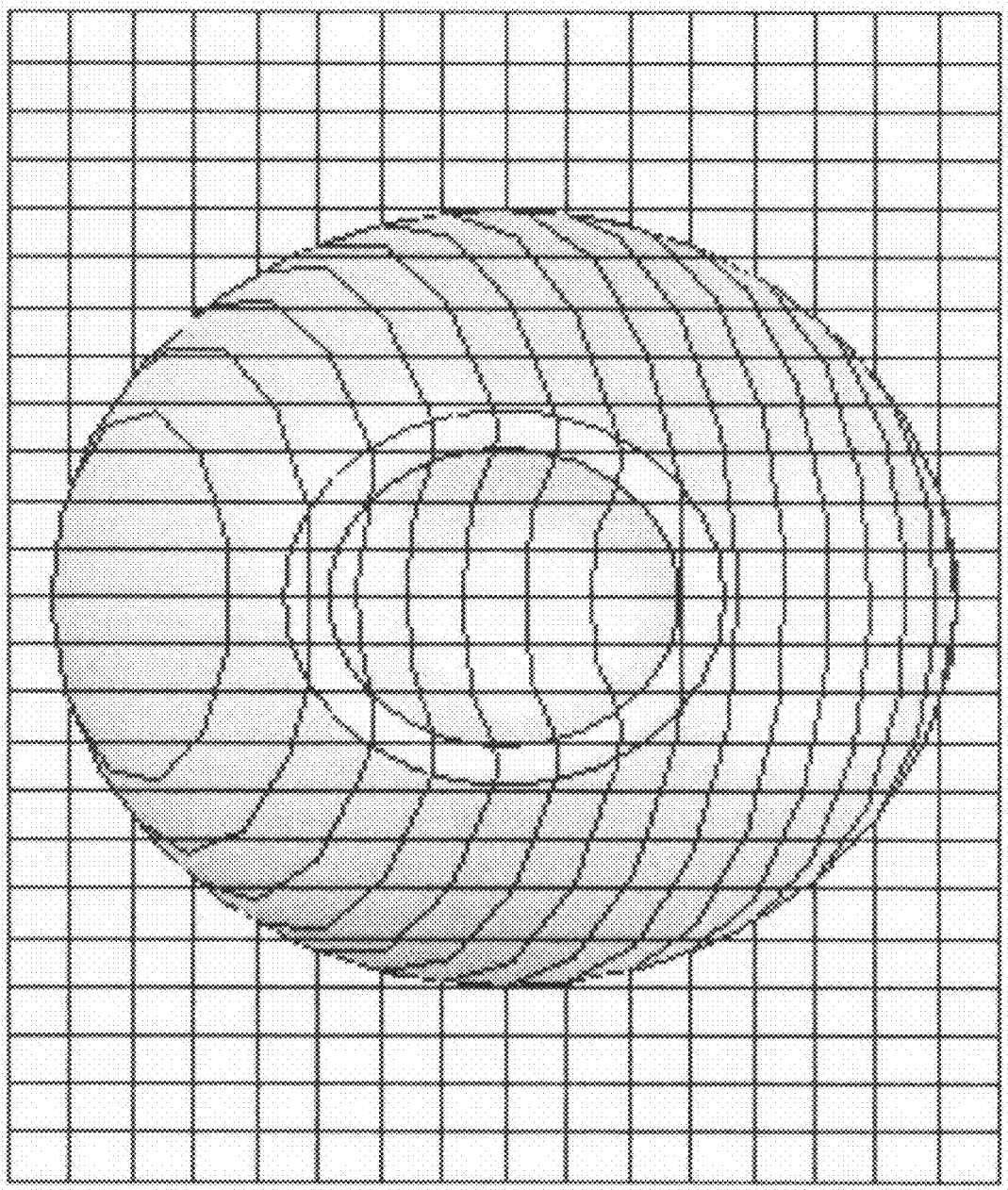
FIG. 5 is a top view of a projected d.RCT grid on a simulated cornea after an air puff deformation of the corneal surface.
Figure 6:
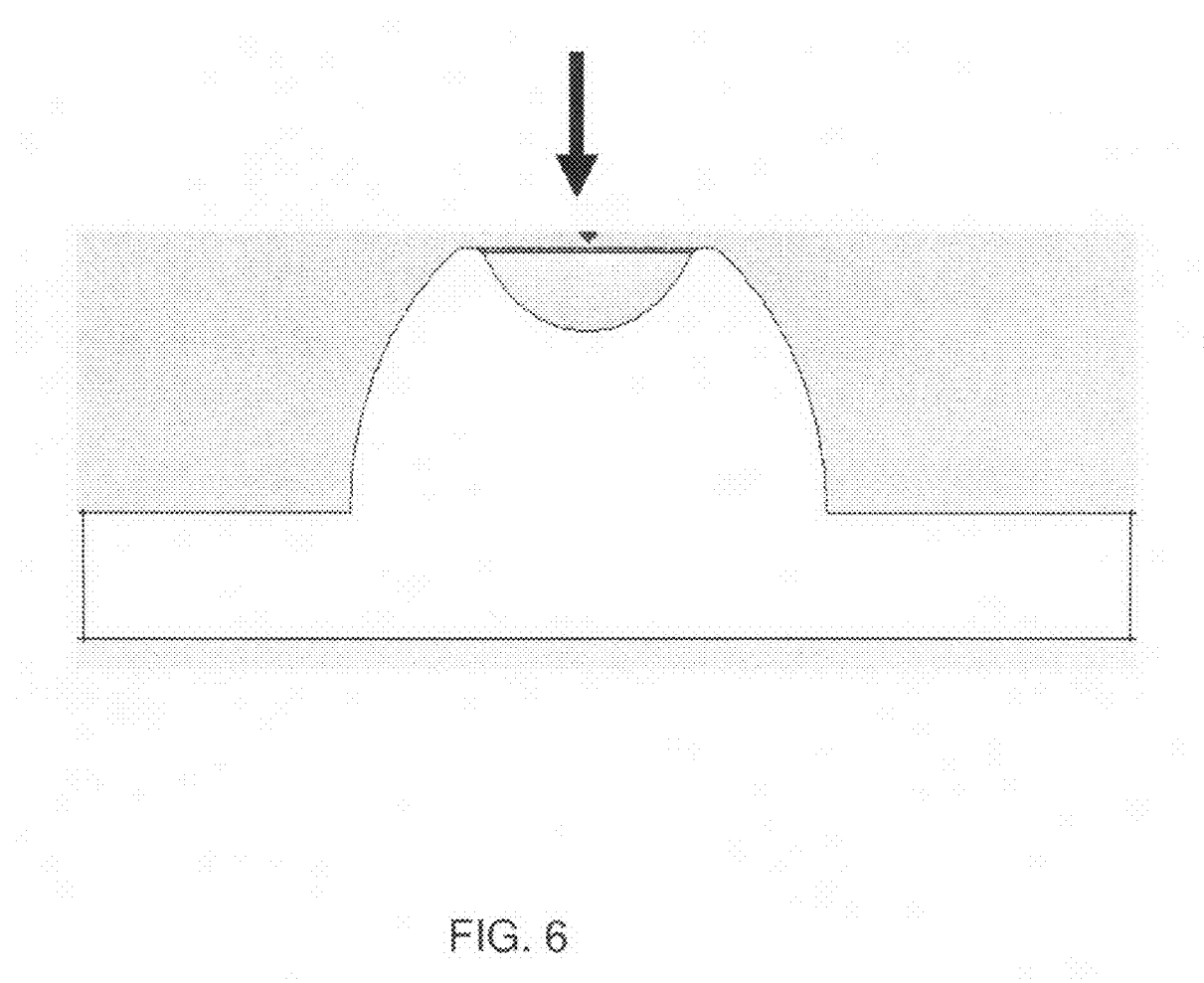
FIG. 6 is a schematic side view of corneal indentation corresponding to the deformation shown in FIG. 5.
Figure 7:
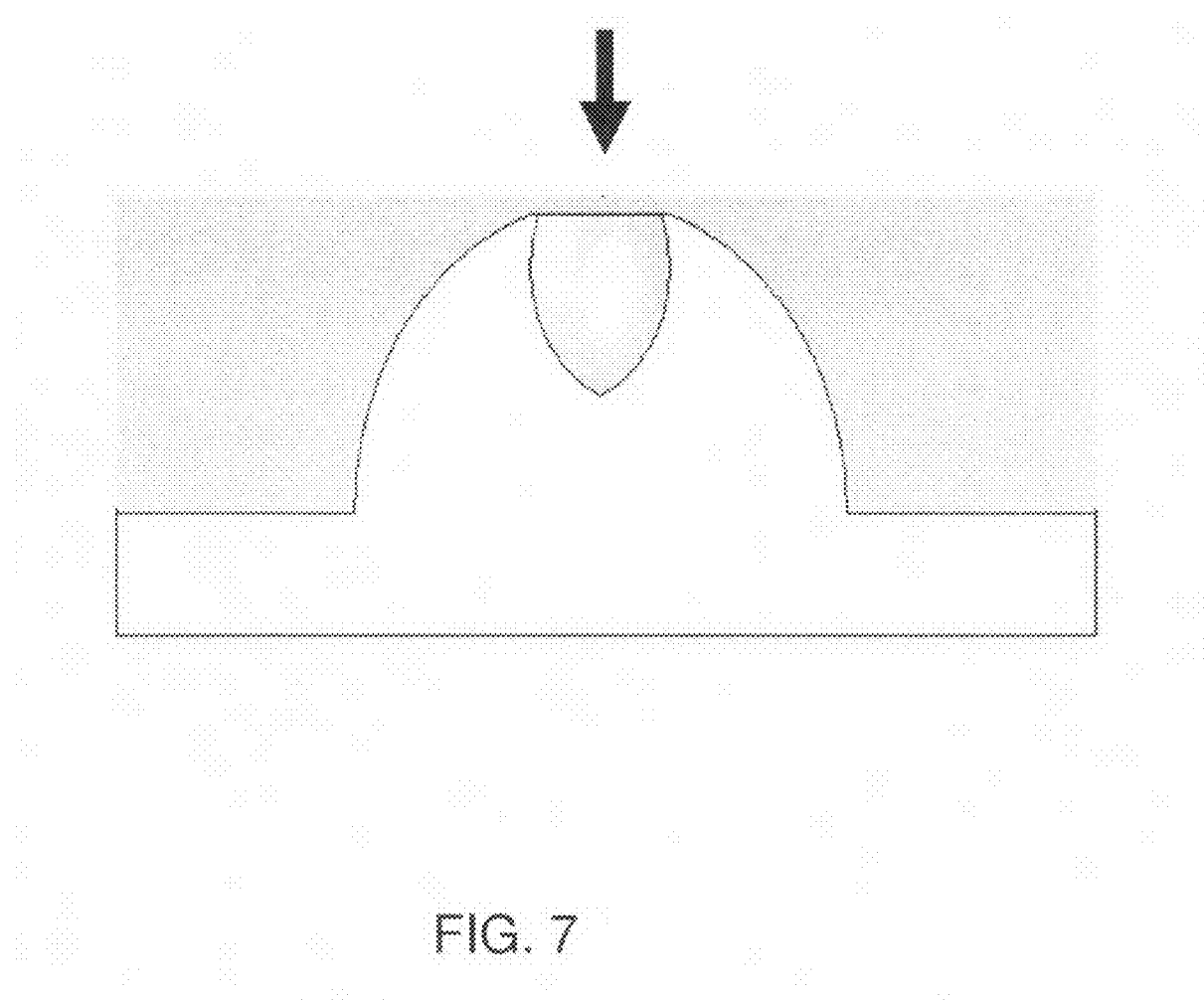
FIG. 7 is a schematic side view of corneal indentation showing a narrower, deeper corneal indentation that that shown in FIG. 6.

As noted above, FIGS. 4 and 5 show simulated d.RCT cornea/grid images before and during, respectively, an air puff deformation of an in-vivo corneal surface. FIG. 6 illustrates a wide, shallow corneal indentation corresponding to that in FIG. 5. For comparative illustration, FIG. 7 shows a narrower and deeper corneal indentation than that shown in FIG. 6. The figures illustrate that softer or stiffer corneas may respond differently to an applied deformation force, due to their different biomechanical and/or biodynamic characteristics.

Figure 15:
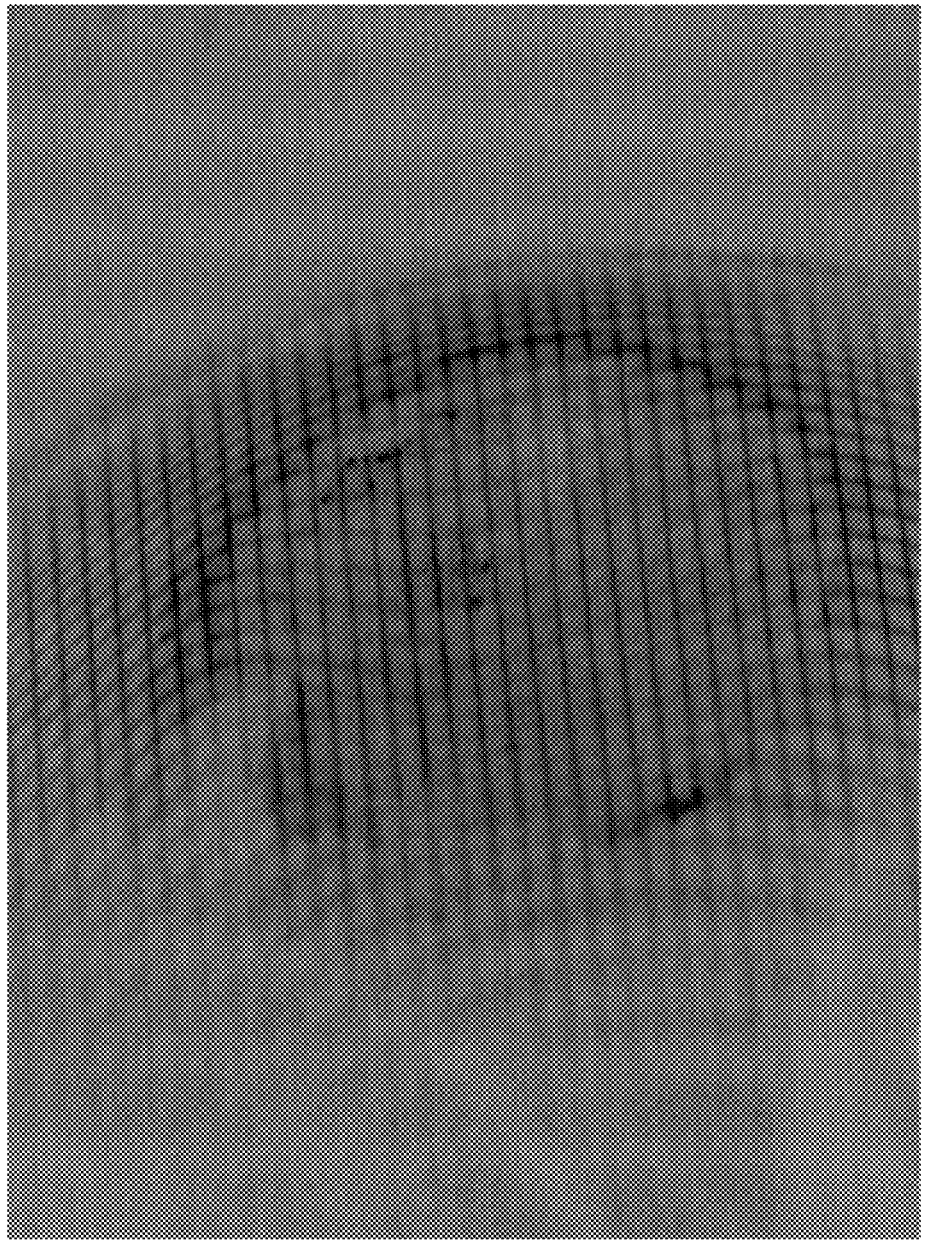
FIG. 15 shows an in-vivo grid image of a deformed cornea, according to an illustrative aspect of the invention.

FIG. 15 shows a d.RCT-based in-vivo cornea/grid image of the instant inventor Roberts' cornea during an air puff-induced deformation interval. The inventor believes that this is the first such in-vivo image ever obtained during a deformation interval, in accordance with an object of the invention.

Figure 16:
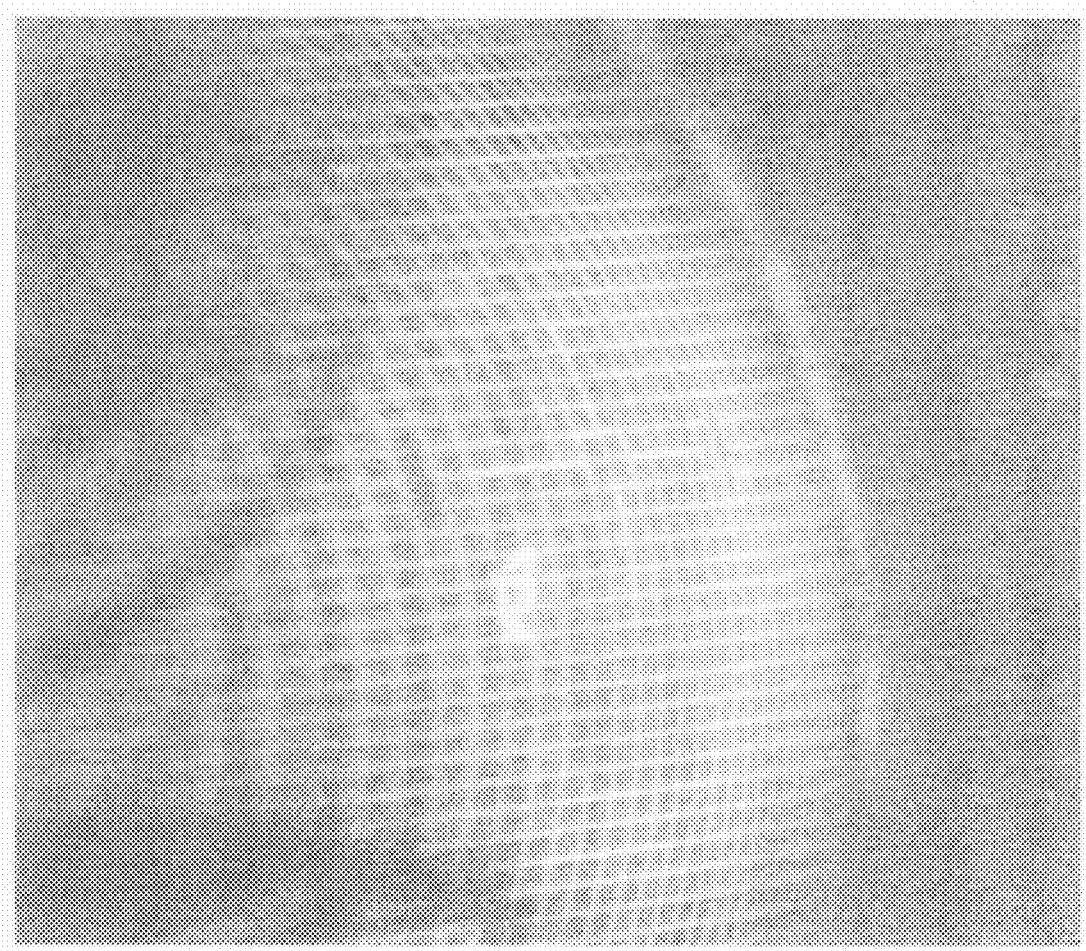
FIG. 16 shows a grid image of an undeformed cornea with a cross hairs projected thereon, according to an illustrative aspect of the invention.

Based upon at least only a single intra-deformation, in-vivo cornea/grid image such as that shown in FIG. 15 and a pre-deformation in-vivo cornea/grid image, as illustrated in FIG. 16, various in-vivo corneal deformation characteristics can be measured, from which biomechanical and biodynamic properties of a living eye can be determined. For example, the surface displacement, symmetry/asymmetry, shape, area of the surface deformation, deformation depth, corneal curvature, elevation, and other selected topographical characteristics of the corneal-scleral region of a live cornea not previously acquirable without the embodied invention, can be measured during the deformation interval allowing the calculation of elastic and viscoelastic characteristics of an in-vivo cornea as described more fully below.

An embodiment of the invention is directed to a method for determining a biomechanical and/or a biodynamic property of an in-vivo cornea. The method generally involves the steps of obtaining at least only a single image of an in-vivo cornea/grid in an undeformed state, which provides quantitative information about selected topographical characteristics of the undeformed in-vivo cornea; controllably deforming the cornea via a known force provided by an air puff over a deformation interval; obtaining at least only a single image of the in-vivo cornea/grid in the deformed state due to the known amount of the force applied during the deformation interval, which provides quantitative information about the selected topographical characteristics of the deformed in-vivo cornea; and using the selected topographical characteristic measurements in the undeformed and deformed states (e.g., spatial displacement of a known point), as well as other appropriate measured (or supplied) data (e.g., IOP) to determine a biomechanical (elastic) and/or a biodynamic (viscoelastic) condition of the in-vivo cornea.

It will be appreciated that the apparatus and methods disclosed herein are also enabled for a non-in-vivo cornea/eye, such as might be obtained, for example, from an eye bank.

Figure 17:
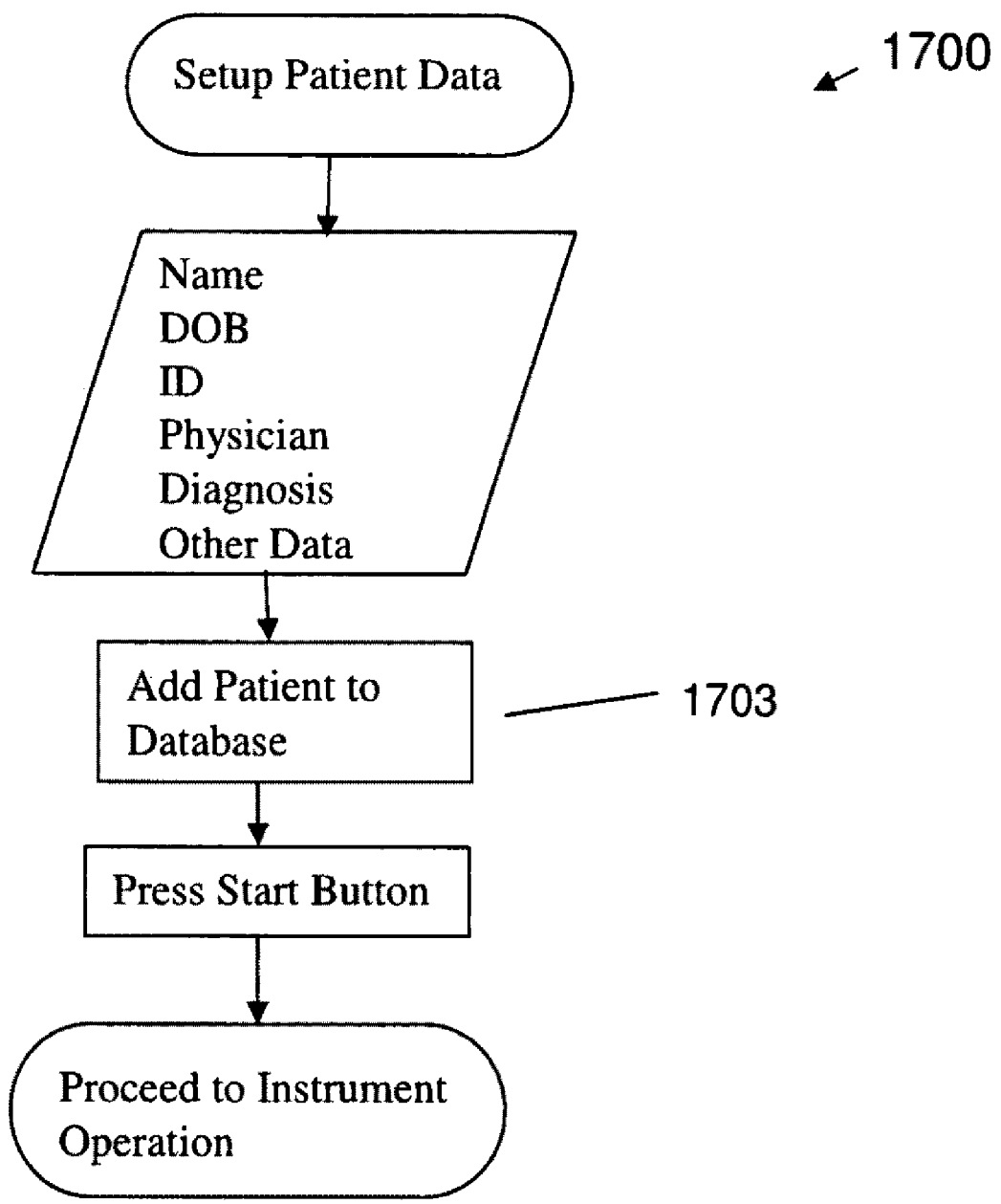
FIGS. 17, 18, and 19 are flow charts showing the steps of the d.RCT device operation and measurement, according to an illustrative aspect of the invention.
Figure 18:
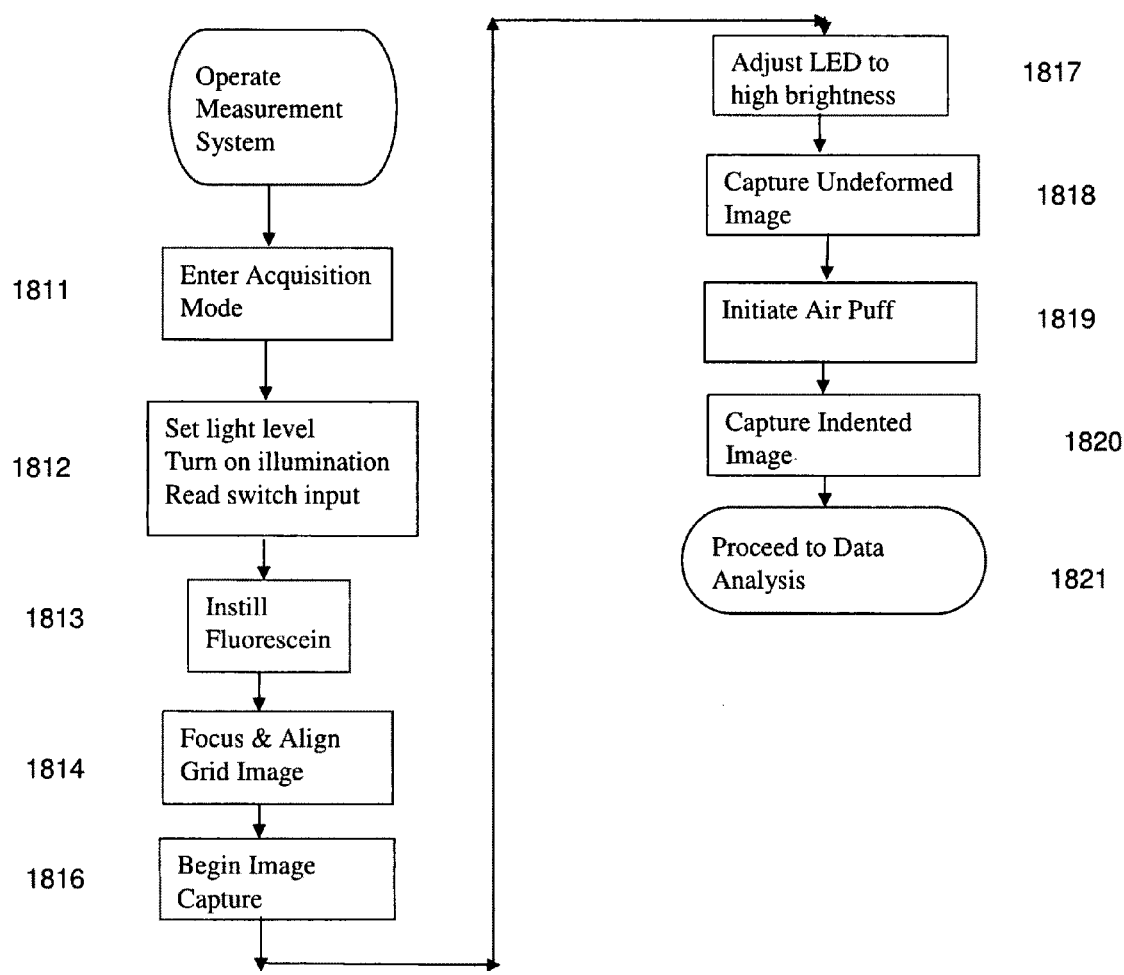
Figure 19:
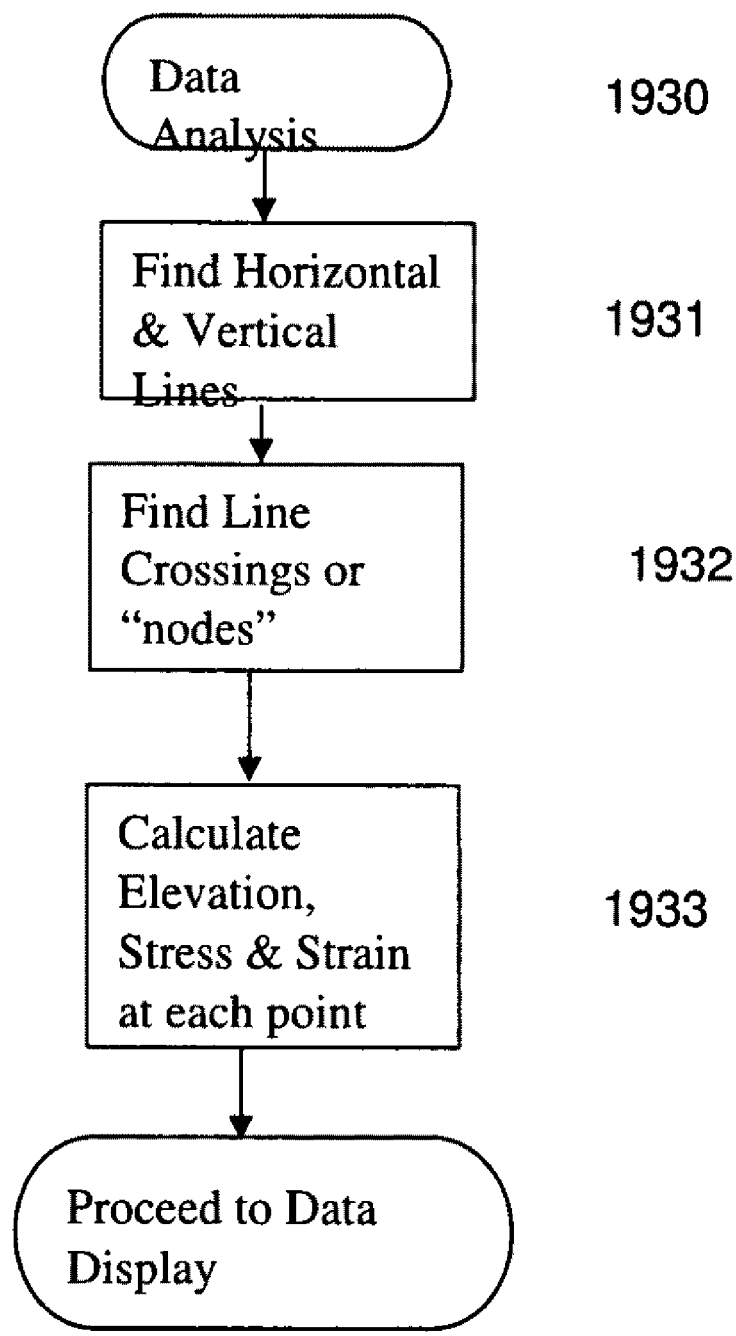

More specifically and in accordance with a non-limiting, illustrative aspect of the invention, and with reference to FIGS. 17, 18, and 19, the method entails the initial setup (step 1700) of the measurement system (FIG. 17). After powering on the system, the operator enters patient data into a database, at step 1703. The patient data may include name, date of birth, unique ID or Social Security number, physician, diagnosis, and any other pertinent data. The operator may then choose to start a new exam and selects which eye will be measured (OD or OS).

Upon successful completion of the initial setup of the measurement system, the system enters acquisition alignment mode at step 1811, FIG. 18. A PC component sends commands to the measurement head via a USB interface. These commands perform the functions (described above) of setting the illumination light level, providing power to the illumination LEDs at the correct light level, and enabling the system to read an input switch, at step 1812. The PC system may then display a live video image of the grid projected onto the cornea on the display. The operator is then ready to instill one or more drops of fluorescein (or other dye) at the appropriate concentration on the eye, at step 1813.

Figure 20:
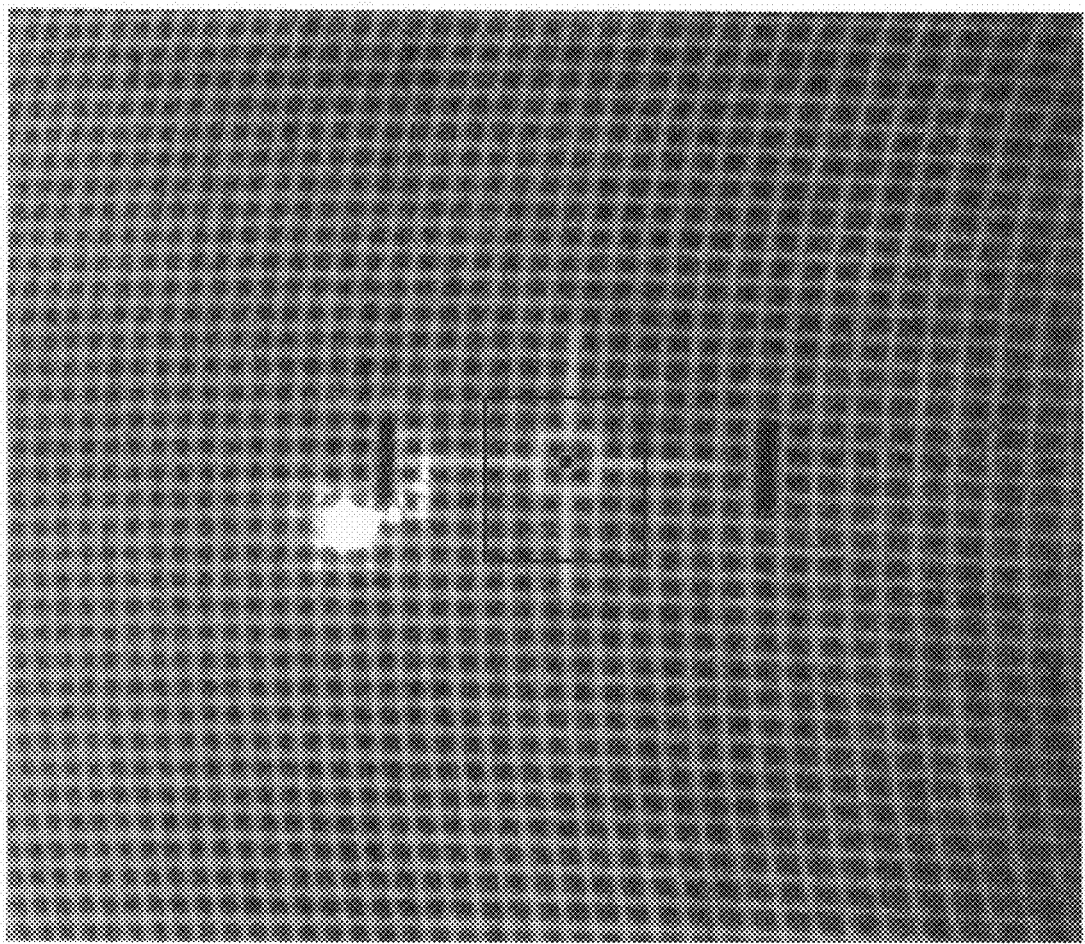
FIG. 20 illustrates an algorithmic result of center finding for the image shown in FIG. 16, according to an illustrative aspect of the invention.

Using a joystick or other method to move the measurement head in relation to the subject's cornea, the operator manipulates the measurement head to place it in the correct orientation. The operator centers the projected grid onto the cornea utilizing cross hairs in the grid reticle as a center reference. The center of the cross hairs are advantageously located at the apex of the cornea, as illustrated in FIG. 20. The operator also moves the measurement head closer to or farther away from the cornea to bring the projected grid into best focus, at step 1814. In an aspect, preliminary alignment is performed by the operator, and subsequent xyz alignment on the corneal apex may be performed automatically by the system. As described above, the measurement grid and the air puff are internally aligned due to the 'operational integration' of the device.

When the best focus has been achieved, a command is triggered to begin acquisition of at least only a single pre-deformation in-vivo cornea/grid topographical characteristic image, at step 1816.

After the software has received the command to acquire the image, a sequence of measurements are initiated. The LEDs of a wavelength chosen to excite the secondary emissions of the fluorescein are turned on at a higher brightness than is used for alignment, at step 1817. An initial image of the grid projected onto the cornea is captured at step 1818 and saved in computer memory. The non-contact surface deformer delivers an air puff that perturbs (deforms) the cornea, at step 1819, causing it initially to indent inward, as shown in FIG. 15. When the system senses that applanation has reached its maximum depth through feedback from the applanation pressure, or upon another selected trigger position, an at least only a single second image of the grid projected onto the in-vivo cornea is acquired, at step 1820, by the CCD element of the digital camera. The acquired digital image is then stored in memory for further analysis, at step 1821. Only a single pre-deformation image and a single intra-deformation image are required to make the necessary topographical characteristic measurements for determining the biomechanical and/or biodynamic properties of the living eye according to the embodied invention. Alternatively, a series of intra-deformation images may be acquired with a high-speed camera in order to obtain multiple, spatially resolved data over the corneal surface.

Using the captured in-vivo cornea/grid images, analysis of the measured data follows (step 1930, FIG. 19). The analysis software first identifies horizontal and vertical lines of the grid, at step 1931, and grid nodes, i.e., points surrounded by intersections of horizontal and vertical lines, at step 1932, using custom algorithms (described below). The x and y (spatial) location of each node is calculated and stored in computer memory. For each node location, a surface elevation value relative to the instrument axis is calculated. Additionally, stress and strain are calculated at each spatial location, at step 1933.

Figure 21:
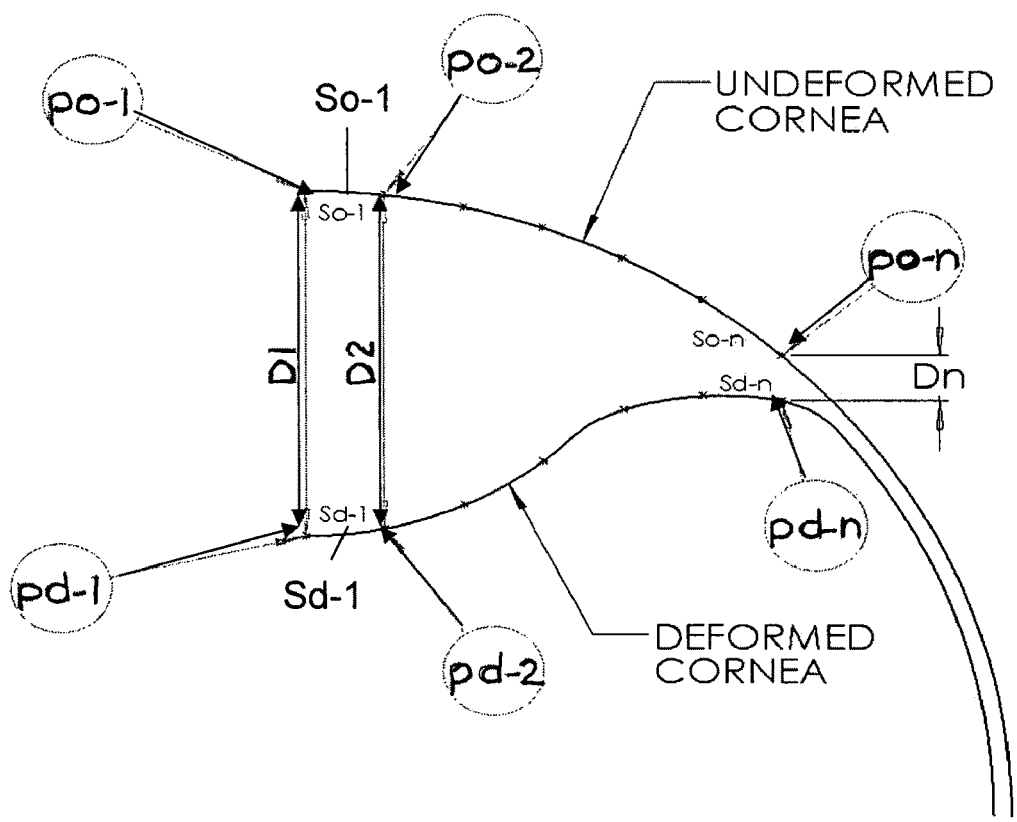
FIG. 21 illustrates a cross sectional schematic of two subsequent rasterstereographic acquisitions, according to an exemplary method embodiment of the invention.

Using the measured shape of a deformed in-vivo cornea perturbed with an air-puff, supplied or measured intraocular pressure data, and the measured elevation data of the cornea both pre-deformation and during deformation, quantitative biomechanical and biodynamic properties of the live cornea can be determined. One exemplary method facilitating such calculations is set forth in Glass et al., *A Viscoelastic Biomechanical Model of the Cornea Describing the Effect of Viscosity and Elasticity on Hysteresis*, Investigative Opthalmology & Visual Science, September 2008, Vol. 49, No. 9, the subject matter of which is incorporated herein by reference in its entirety to the fullest allowable extent. FIG. 21 illustrates a cross sectional schematic of two subsequent rasterstereographic acquisitions, one of the cornea pre-deformation and one of the cornea deformed under an air-puff. Utilizing a rasterstereographic topographical system, grid points are captured on each surface and the three-dimensional spatial locations (xyz) of each point are recovered. The Points po-1 through po-n represent grid intersections on the undeformed cornea and points pd-1 through pd-n represent the corresponding points on the deformed cornea. Segment lengths So-1 through So-n correspondingly represent corneal segment lengths between adjacent grid intersection points and segments Sd-1 through Sd-n represent corneal segment lengths between the corresponding intersection points on the deformed cornea. Distances D1 through Dn represent the depth of the depression at the corresponding grid points.

Given this model, and utilizing corneal pachymetry data, the strain (ε) of any segment can be calculated from the measured deformed and undeformed segment lengths utilizing the equation $$\varepsilon = \frac{S_d n - S_o n}{S_o n}.$$

Stress, σ, at any point on the cornea can be calculated using Laplace's law where $$\sigma = \frac{IOP \cdot R_{curve}}{2 \cdot t}.$$

IOP can be determined from the air puff force (e.g., by the d.RCT or otherwise provided), radius of curvature ($R_{curve}$) is calculated at each point by the d.RCT software, and corneal thickness at each point (t) can be input from a pachymetry instrument.

Using stress-strain calculations, elasticity and viscosity can be calculated using the model of Glass et. al. Thus the Glass et al. model would allow one to obtain an overall corneal value for elasticity and viscosity using the embodied apparatus.

In a non-limiting, illustrative aspect of the instant invention, a novel approach to determining quantitative biomechanical and biodynamic properties of an in-vivo cornea includes the steps of measuring corneal stiffness, k, on a point by point (grid intersection by grid intersection) manner. Stiffness is a measure of the resistance offered by the body to bending and is defined as k=P/δ, where P is the applied force and δ is the resulting displacement. The force is provided by knowledge of the characteristics of the air puff and the displacement will be provided by the d.RCT in measurements of $\delta_{Pre\text{-}def}$ and $\delta_{During\text{-}def}$. This measurement may be calculated completely with data provided by the d.RCT as described herein. Such measurements can provide, in contrast to the Glass et al. approach, multiple (e.g., hundreds or more) of spatially resolved, in-vivo values over the selected corneal region, thus allowing one to obtain heretofore unmeasurable biomechanical and biodynamic information across the in-vivo corneal surface.

An image processing algorithm that involves process steps for determining the in-vivo topography of a corneo-scleral surface with the d.RCT described herein above is set forth below as follows.

Figure 22:
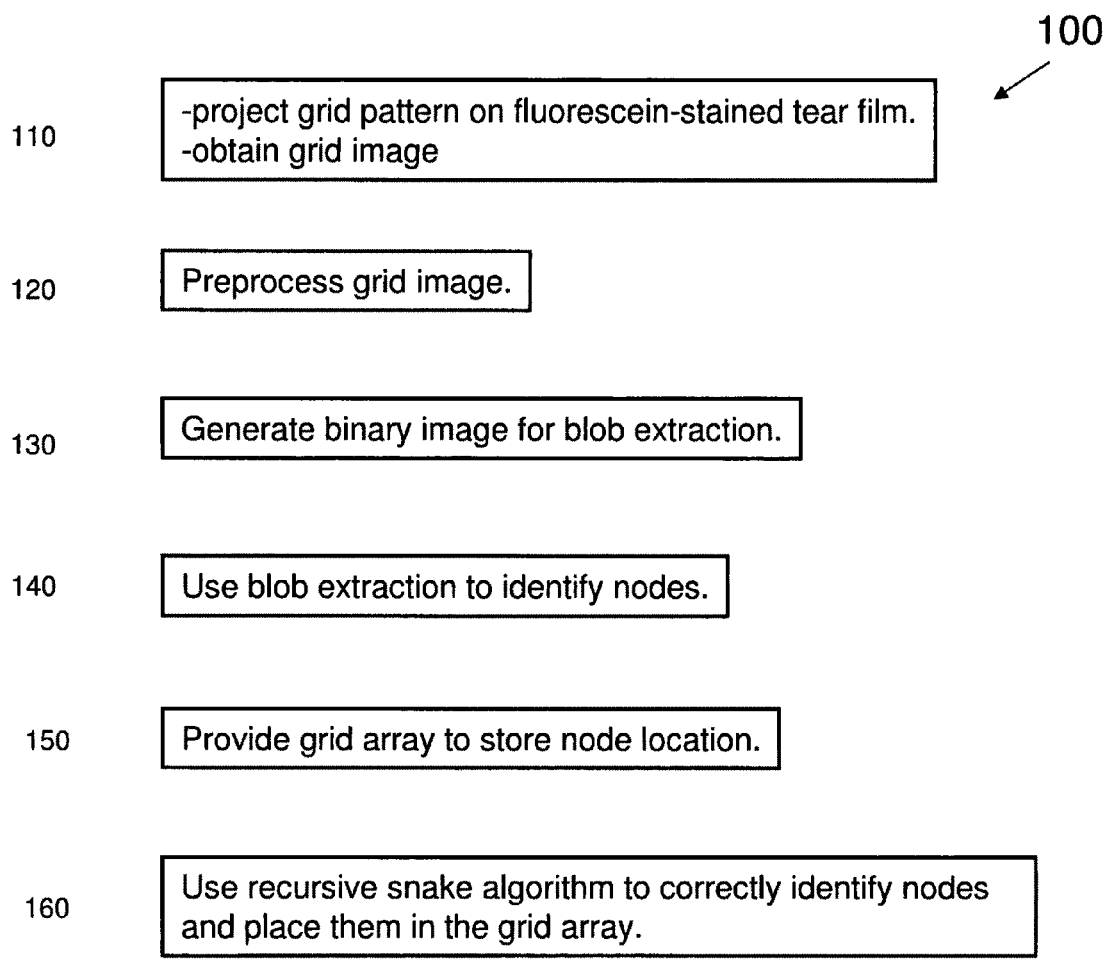
FIG. 22 is a flow chart showing the process steps of an image processing method, according to an exemplary aspect of the invention.

The process steps 100 of the image processing method are outlined in FIG. 22. In general terms, the process 100 allows one to extract the grid features from an advanced rasterstereography-based corneo-scleral topography (d.RCT) system-captured grid image. Once the features have been extracted, the target surface topography can be reconstructed and displayed. It is particularly advantageous that the total time for processing the image can be less than 2.0 seconds. In an exemplary aspect, the processing time for the algorithm running on a 3 GHz PC is about 0.2 seconds.

Figure 23:
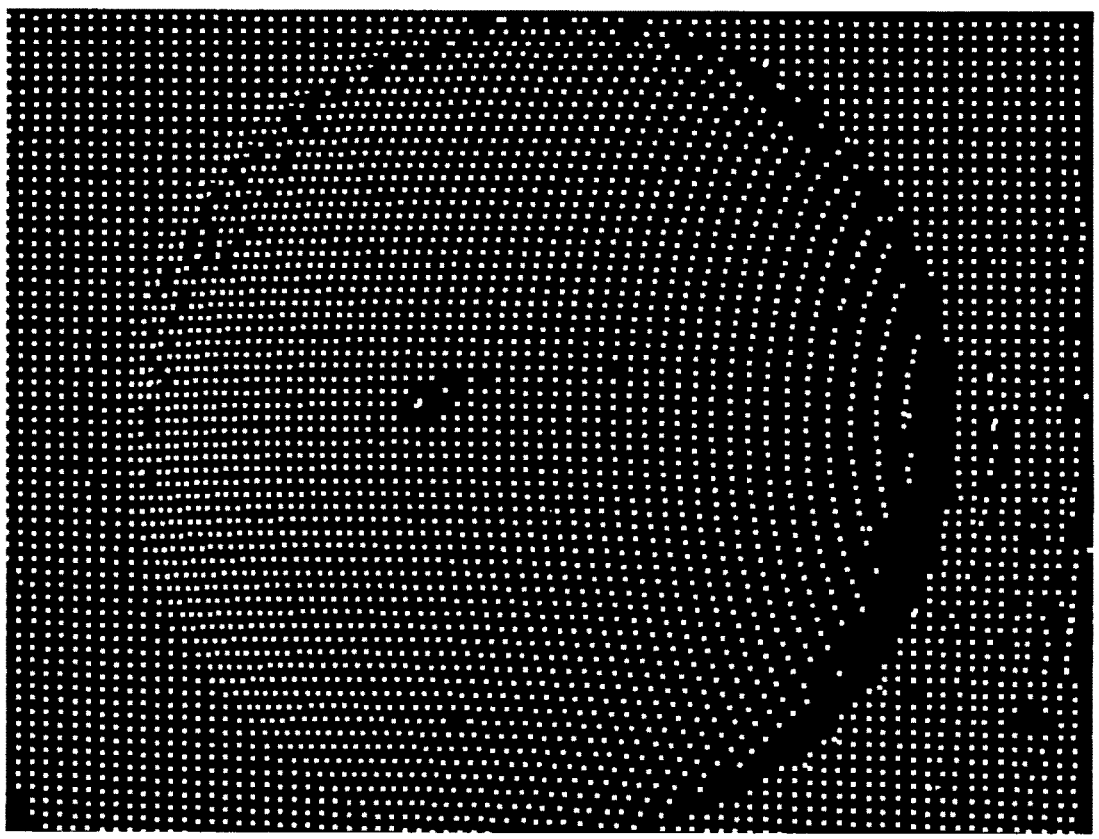
FIG. 23 shows a node image of the cornea according to an illustrative aspect of the invention.

At step 110, an exemplary cyan grid pattern is projected onto a fluorescein-stained tear film of a corneo-scleral surface to be measured, and an image of the fluorescing grid 205 is obtained, as illustrated in FIG. 16. The task at hand is to find the center of the grid and all grid intersections in the image. A node, as that term is used herein, is defined as the pixel space bounded by four associated intersection points of horizontal and vertical lines of the grid image. FIG. 23 shows a node image.

Step 120 involves preprocessing of the captured imaged in order to enhance image structures.

Step 130 involves producing a binary image from which nodes locations can be extracted.

At step 140, a blob extracting routine is used to identify nodes and record their locations.

At step 150, a two dimensional grid array is provided to store node locations in their corresponding grid locations. A starting node is selected and its location is stored at the center of the grid array.

At step 160, a recursive snake algorithm (see FIG. 24) is used to identify subsequent nodes and properly place them in the grid array.

The image processing algorithm details will now be described.

Figure 25:
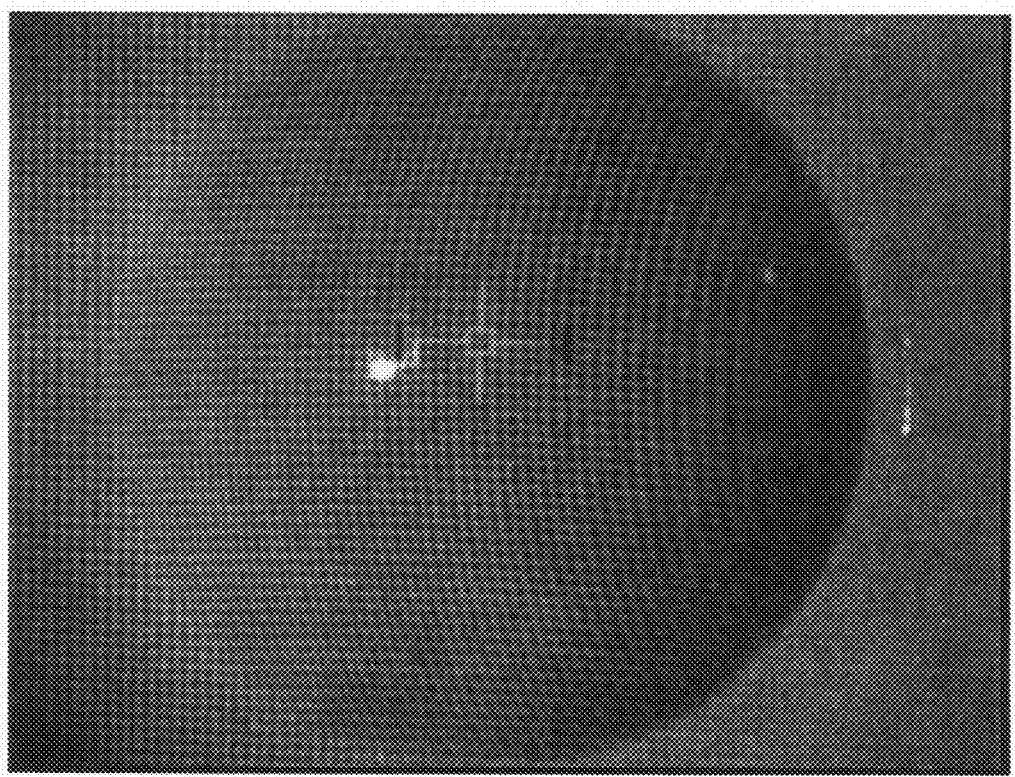
FIG. 25 illustrates a two dimensional Gaussian smooth applied to a raw captured image, according to an illustrative aspect of the invention.

A two dimensional Gaussian smooth is applied to the raw captured image, as shown in FIG. 25. Gaussian smoothing is used as a pre-processing stage in computer vision algorithms in order to enhance image structures. A Gaussian smooth in one dimension is equivalent to convolving the image with a Gaussian function.

$$G(x) = \frac{1}{\sqrt{2\pi\sigma^2}} e^{-\frac{x^2}{2\sigma^2}}$$

In two dimensions, it is the product of two Gaussians, one for each direction.

$$G(x, y) = \frac{1}{\sqrt{2\pi\sigma^2}} e^{-\frac{x^2+y^2}{2\sigma^2}}$$

Figure 26:
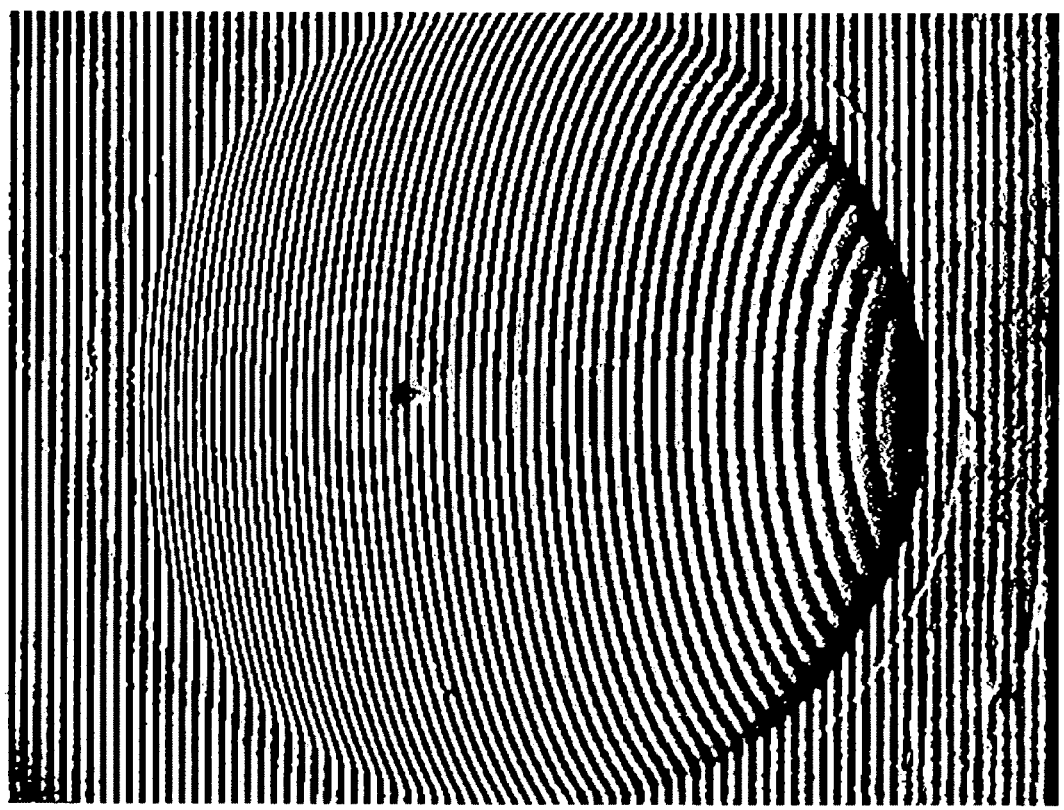
FIGS. 26 and 27 show $1^{st}$ derivative images of the smoothed image taken in the X and Y direction, respectively, according to an illustrative aspect of the invention.
Figure 27:
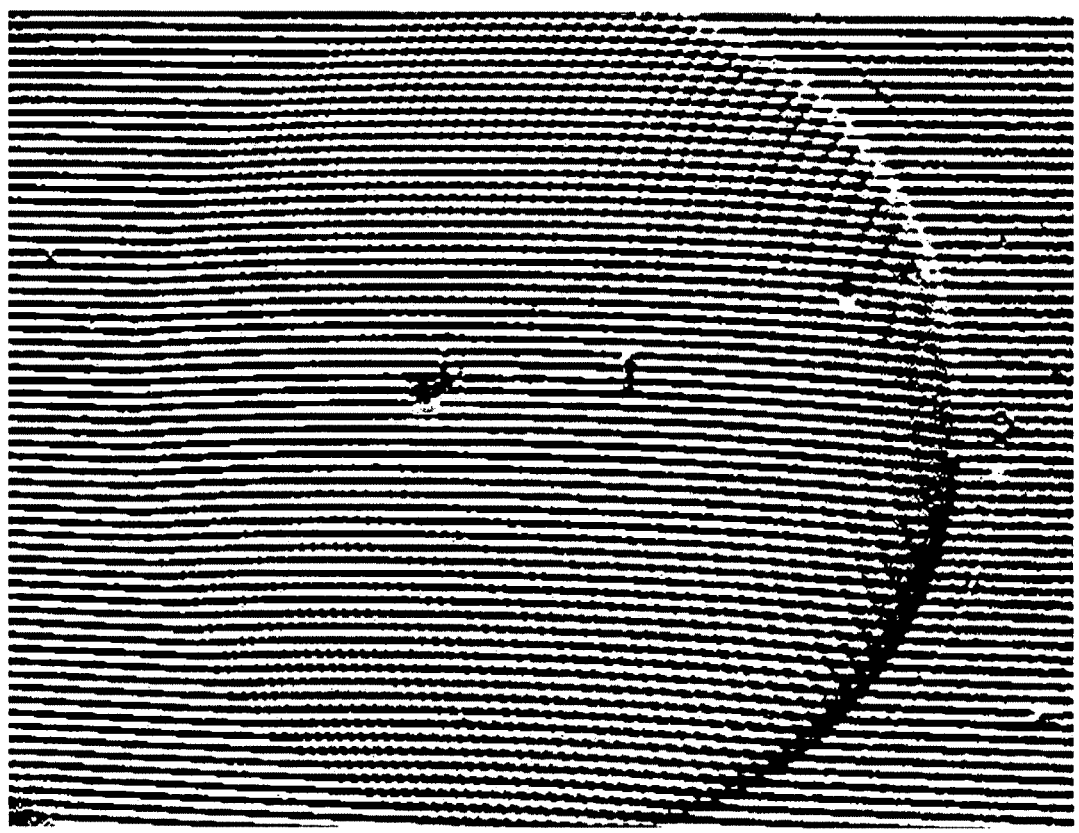

Next, first derivative images of the smoothed image are produced, as shown in FIGS. 26 and 27. The derivatives are taken in the X and Y direction. These images represent the rate of change of intensity values in each direction.

Figure 28:
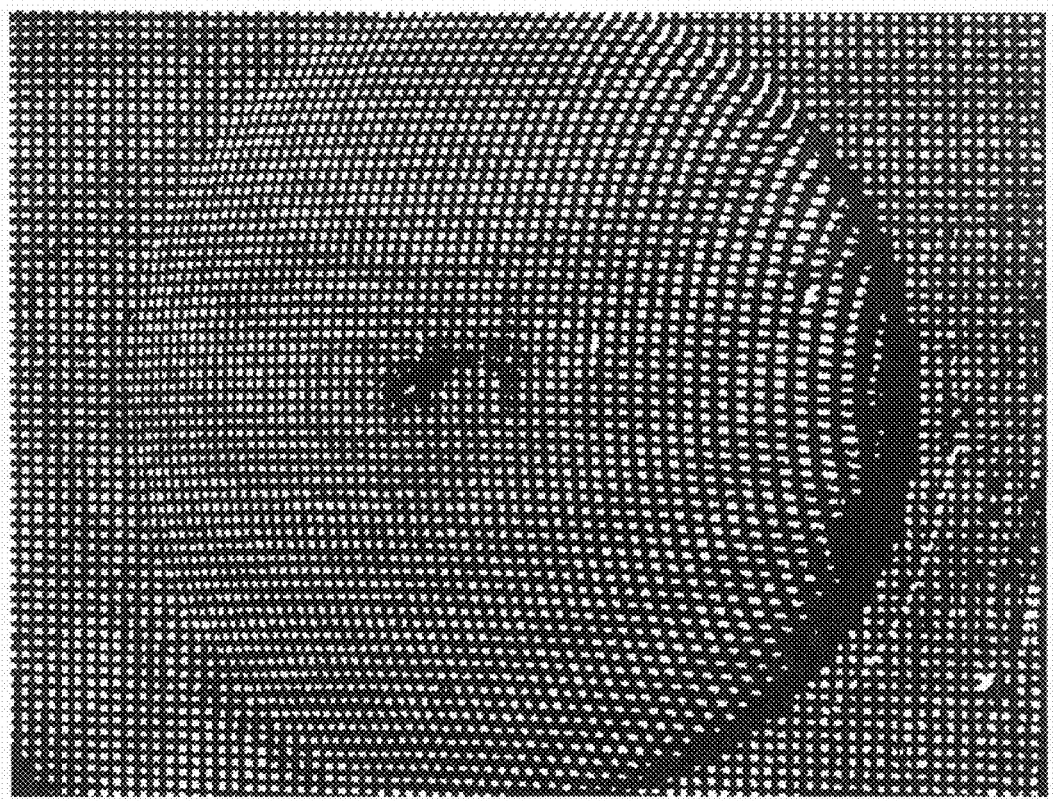
FIG. 28 shows a single Magnitude image from the two combined derivative images, according to an illustrative aspect of the invention.

The two first derivative images are then combined into a single Magnitude image (FIG. 28). The magnitude is calculated as:

Magnitude=$\sqrt{Dx^2+Dy^2}$ on a point by point basis. The Magnitude image is then thresholded to produce a black and white binary image. This binary image is used to identify 'blobs,' which represent the nodes to be extracted. A 'blob' is a region in an image that is brighter than its surroundings.

A blob extracting routine is used to identify blobs in the Magnitude image and record the coordinates of the blobs. Blob extraction is an image segmentation technique that categorizes the pixels in an image as belonging to one of many discrete regions. Blob extraction is generally performed on the resulting binary image from a thresholding step. The coordinates for each blob are used as their initial locations.

Figure 29:
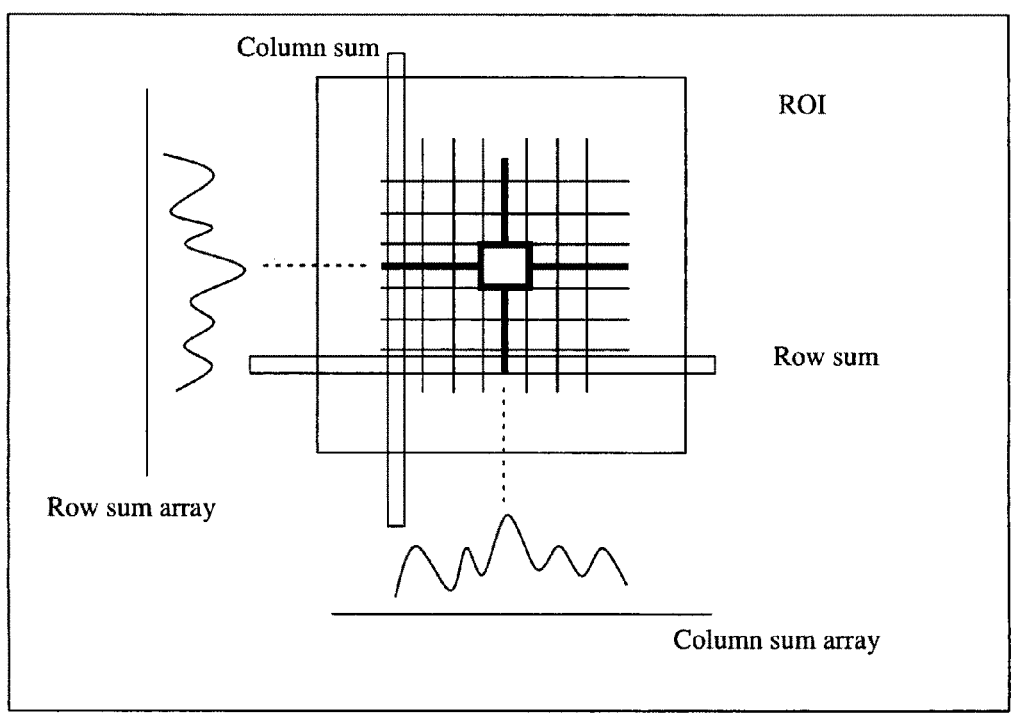
FIG. 29 is a schematic diagram useful in illustrating how row and column sums are used to find the location of the center of grid pattern, according to an illustrative aspect of the invention.
Figure 30:
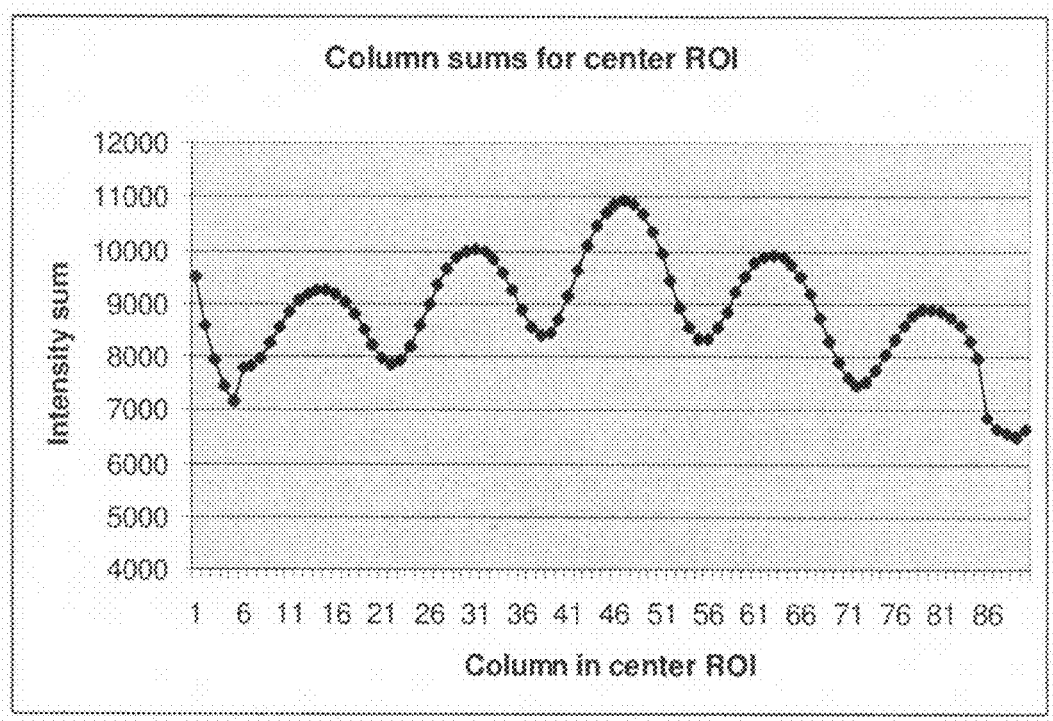
FIG. 30 illustrates a profile of column sums in a region of interest (ROI) for the image shown in FIG. 16, according to an illustrative aspect of the invention.

All node locations are refined using the original raw data by using histograms of row and column sums around each node location, as shown in FIG. 29. The cross pattern defining a node is brighter and has a higher contrast than surrounding pixels. The sums of all pixels along a row inside a region of interest (ROI) around a node location are saved in a row sum array. The same procedure is carried out for the columns in the ROI for a column sum array, as shown in FIG. 30. Once the row and column sums are found, the peaks are found in the arrays as the maximum values. The peak in the row sum array corresponds to the y-location of the node, and the peak in the column sum array corresponds to the x-location of the node.

Figure 24:
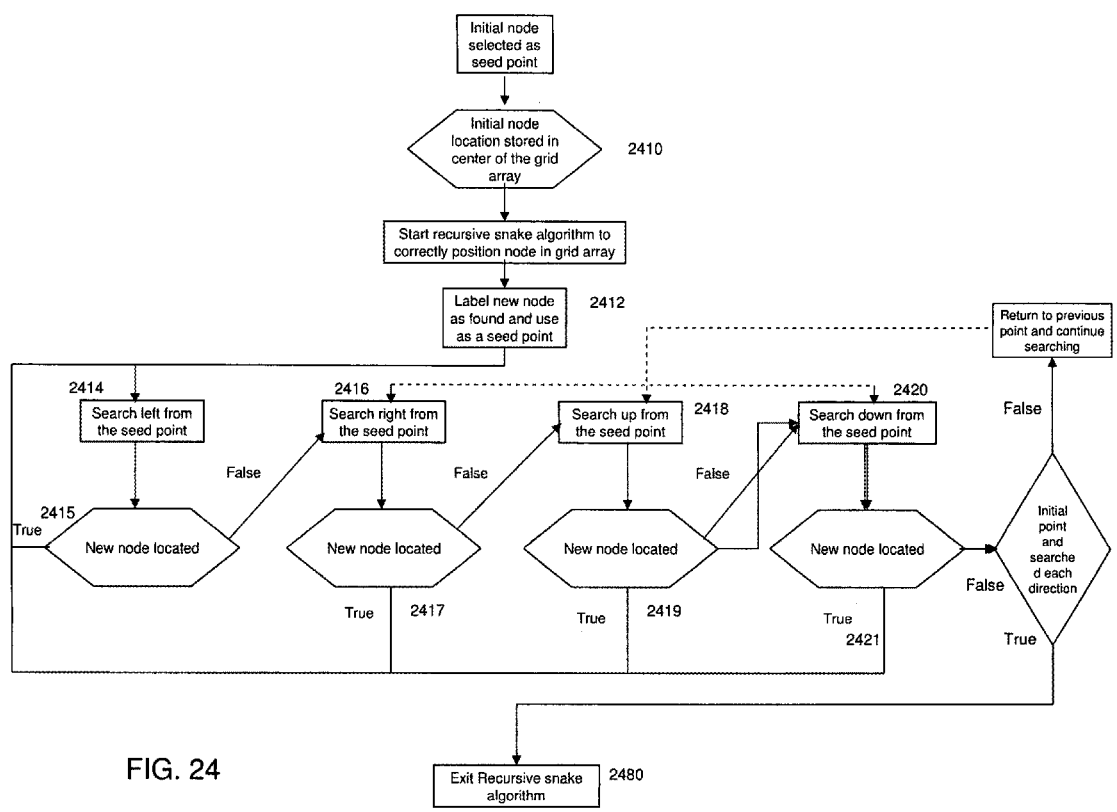
FIG. 24 is a flow chart showing the process steps of a recursive snake algorithm used to identify subsequent nodes and properly place them in the grid array, according to an illustrative aspect of the invention.

To correctly position each node in the grid array, a recursive snake algorithm is used as illustrated in FIG. 24. The initial seed point from step 150 (FIG. 22) is stored at the center of the grid array at step 2410. The node is labeled and used to prevent later "finding". The steps of the recursive algorithm are as follows.

Step 2412: Label the seed point as used to prevent later "finding".

Step 2414: From the seed point, search left.

If the left search finds a new node (2415) update left search prediction parameters based on the position of point to the right.

Place node coordinates in correct location of the 2-D grid.
Repeat from step 2412 with the new node as a seed.

Step 2416: From the seed point, search right.

If the right search finds a new node (2417) update right search prediction parameters based on the position of point to the left.

Place node coordinates in correct location of the 2-D grid.
Repeat from step 2412 with the new node as a seed.

Step 2418: From the seed point, search up.

If the up search finds a new node (2419) update up search prediction parameters based on the position of point below.

Place node coordinates in correct location of the 2-D grid.
Repeat from step 2412 with the new node as a seed.

Step 2420: From the seed point, search down.

If the down search finds a new node (2421) update down search prediction parameters based on the position of point above.

Place node coordinates in correct location of the 2-D grid.
Repeat from step 2412 with the new node as a seed.

Step 2480: The algorithm finishes when no further new nodes can be located.

While the above described exemplary processing algorithm is fast and reasonably robust, it is anticipated that certain image artifacts may cause errors that could propagate through the reconstruction processing to yield a surface representation that is not correct in certain areas of the image. The effects of these errors can be mitigated by the use of a post-processing step that looks for neighbors that appear to be too close, too far, or at too big an angle, with respect to neighbors, as one skilled in the art would appreciate. Once a neighborhood with artifacts such as these are found, the nodes can be deleted by setting the node value to Point (0,0). An editor may also be provided to allow automatic or manual removal of the problem nodes.

The above-described, non-limiting embodiments and aspects of the invention utilized a grid reticle employing uniform, fixed-spaced, rectangular grid geometry. According to alternative, exemplary aspects, non-fixed-spaced, non-rectangular grids may be utilized. As used herein, the term 'square' or 'rectangular' grid means that the 'boxes' formed between the grid intersections are rectangular. As used herein, the term 'warped' grid means that the grid lines become curved and the boxes are no longer rectangles with straight sides.

A warped grid will facilitate increased grid spacing at the cornea; that is, a square grid projected onto a curved surface results in some grid intersections being closer together than others. However, starting with a grid as it would appear on a sphere and then projecting that pattern onto a sphere will produce what looks like a square grid on the sphere. The resulting increased grid intersection spacing may make it easier to image process and may produce a greater number of grid intersections as intersections may now not be overlapping.

In a conventional instrument utilizing a square grid, such as the PAR CTS, the spacing between any two grid intersections is always constant. According to an aspect, a variable line spacing may be provided, giving a denser grid at the center of the cornea and a coarser grid at the periphery. This will increase the resolution of the elevation calculation at the center of the cornea, since the finer grid gives more points in the center. A constantly increasing grid spacing reduces or eliminates a sharp transition in grid density.

Figure 31:
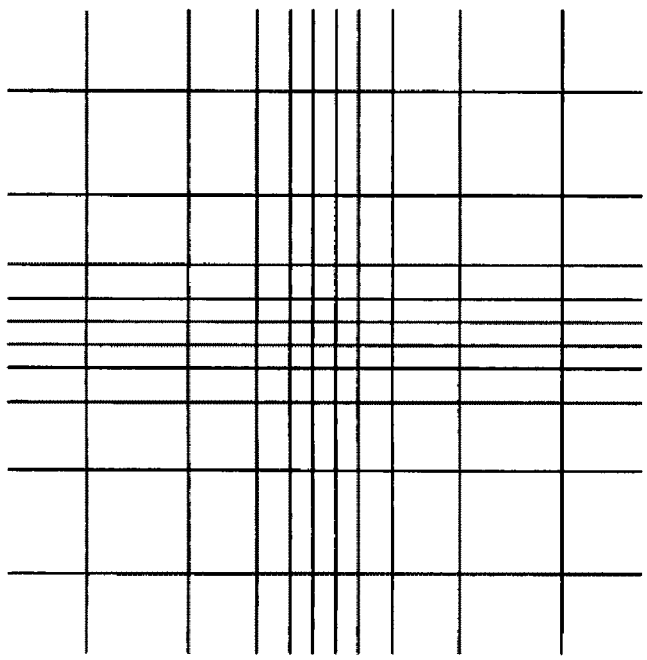
FIG. 31 is a schematic sketch of a non-uniformly spaced grid according to an illustrative aspect of the invention.

FIG. 31 illustrates an exemplary non-fixed-spacing grid pattern 3000 having a constantly increasing (from center) Cartesian (horizontal and vertical) line spacing, which results in higher density along the horizontal and vertical meridians and lowest density at 45 degree meridians. The parameters for this illustrative design are summarized as follows:

Spacing:
Center: 0.075 mm
Peripheral: 0.15 mm
Reticle diameter: 12.5 mm
Line width: 0.006 mm
Pattern: Positive grid chrome-on-glass
Camera to projector angle: 14.25 degrees An illustrative method of determining the spacing between lines at each line starting in the center follows. Given the parameters above, an initial guess was generated using a linear line fit. From this fit, the grid spacing was further refined utilizing an arithmetic progression. The output of this calculation was a dx term representing the spacing between progressive line centers and an absolute position from the grid origin. The factorial term (0.00137) was optimized for the final grid line to fall as close as possible to 0.15 mm spacing at a radius of 6.25 mm. These calculations are shown in Table 1 on the following page.

TABLE 1

| Line # | y start | dx | | x-position |
|---|---|---|---|---|
| 1 | 0.075 | 0.00137 | 0.075 | 0.075 |
| 2 | 0.075 | 0.00137 | 0.07637 | 0.15137 |
| 3 | 0.075 | 0.00137 | 0.07774 | 0.22911 |
| 4 | 0.075 | 0.00137 | 0.07911 | 0.30622 |
| 5 | 0.075 | 0.00137 | 0.08046 | 0.3687 |
| 6 | 0.075 | 0.00137 | 0.08185 | 0.47055 |
| 7 | 0.075 | 0.00137 | 0.08322 | 0.5637 |
| 8 | 0.075 | 0.00137 | 0.08459 | 0.63836 |
| 9 | 0.075 | 0.00137 | 0.08596 | 0.72432 |
| 10 | 0.075 | 0.00137 | 0.08733 | 0.61165 |
| 11 | 0.075 | 0.00137 | 0.0687 | 0.90035 |
| 12 | 0.075 | 0.00137 | 0.09007 | 0.99042 |
| 13 | 0.075 | 0.00137 | 0.09144 | 1.08186 |
| 14 | 0.075 | 0.00137 | 0.09281 | 1.17467 |
| 15 | 0.075 | 0.00137 | 0.09418 | 1.26885 |
| 16 | 0.075 | 0.00137 | 0.09555 | 1.3644 |
| 17 | 0.075 | 0.00137 | 0.09692 | 1.46132 |
| 18 | 0.075 | 0.00137 | 0.09629 | 1.55961 |
| 19 | 0.075 | 0.00137 | 0.09966 | 1.65927 |
| 20 | 0.075 | 0.00137 | 0.10103 | 1.7603 |
| 21 | 0.075 | 0.00137 | 0.1024 | 1.8627 |
| 22 | 0.075 | 0.00137 | 0.10377 | 1.96647 |
| 23 | 0.075 | 0.00137 | 0.10514 | 2.07161 |
| 24 | 0.075 | 0.00137 | 0.10651 | 2.17612 |
| 25 | 0.075 | 0.00137 | 0.10788 | 2.286 |
| 26 | 0.075 | 0.00137 | 0.10925 | 2.39525 |
| 27 | 0.075 | 0.00137 | 0.11062 | 2.50587 |
| 28 | 0.075 | 0.00137 | 0.11199 | 2.61786 |
| 29 | 0.075 | 0.00137 | 0.11336 | 2.73122 |
| 30 | 0.075 | 0.00137 | 0.11473 | 2.84595 |
| 31 | 0.075 | 0.00137 | 0.1161 | 2.96205 |
| 32 | 0.075 | 0.00137 | 0.11747 | 3.07952 |
| 33 | 0.075 | 0.00137 | 0.11884 | 3.19836 |
| 34 | 0.075 | 0.00137 | 0.12021 | 3.31857 |
| 35 | 0.075 | 0.00137 | 0.12158 | 3.44015 |
| 36 | 0.075 | 0.00137 | 0.12295 | 3.5631 |
| 37 | 0.075 | 0.00137 | 0.12432 | 3.68742 |
| 38 | 0.075 | 0.00137 | 0.12569 | 3.81311 |
| 39 | 0.075 | 0.00137 | 0.12705 | 3.94017 |
| 40 | 0.075 | 0.00137 | 0.12843 | 4.0686 |
| 41 | 0.075 | 0.00137 | 0.1298 | 4.1984 |
| 41 | 0.075 | 0.00137 | 0.13117 | 4.32957 |
| 43 | 0.075 | 0.00137 | 0.13254 | 4.46211 |
| 44 | 0.075 | 0.00137 | 0.13391 | 4.59602 |
| 45 | 0.075 | 0.00137 | 0.13528 | 4.7313 |
| 46 | 0.075 | 0.00137 | 0.13665 | 4.86795 |
| 47 | 0.075 | 0.00137 | 0.13802 | 5.00597 |
| 48 | 0.075 | 0.00137 | 0.13939 | 5.14536 |
| 49 | 0.075 | 0.00137 | 0.14076 | 5.28612 |
| 50 | 0.075 | 0.00137 | 0.14213 | 5.42825 |
| 51 | 0.075 | 0.00137 | 0.1435 | 5.57175 |
| 52 | 0.075 | 0.00137 | 0.14487 | 5.71662 |
| 53 | 0.075 | 0.00137 | 0.14624 | 5.86286 |
| 54 | 0.075 | 0.00137 | 0.14761 | 6.01047 |
| 55 | 0.075 | 0.00137 | 0.14896 | 6.15945 |
| 56 | 0.075 | 0.00137 | 0.15035 | 6.3098 |

Figure 32:
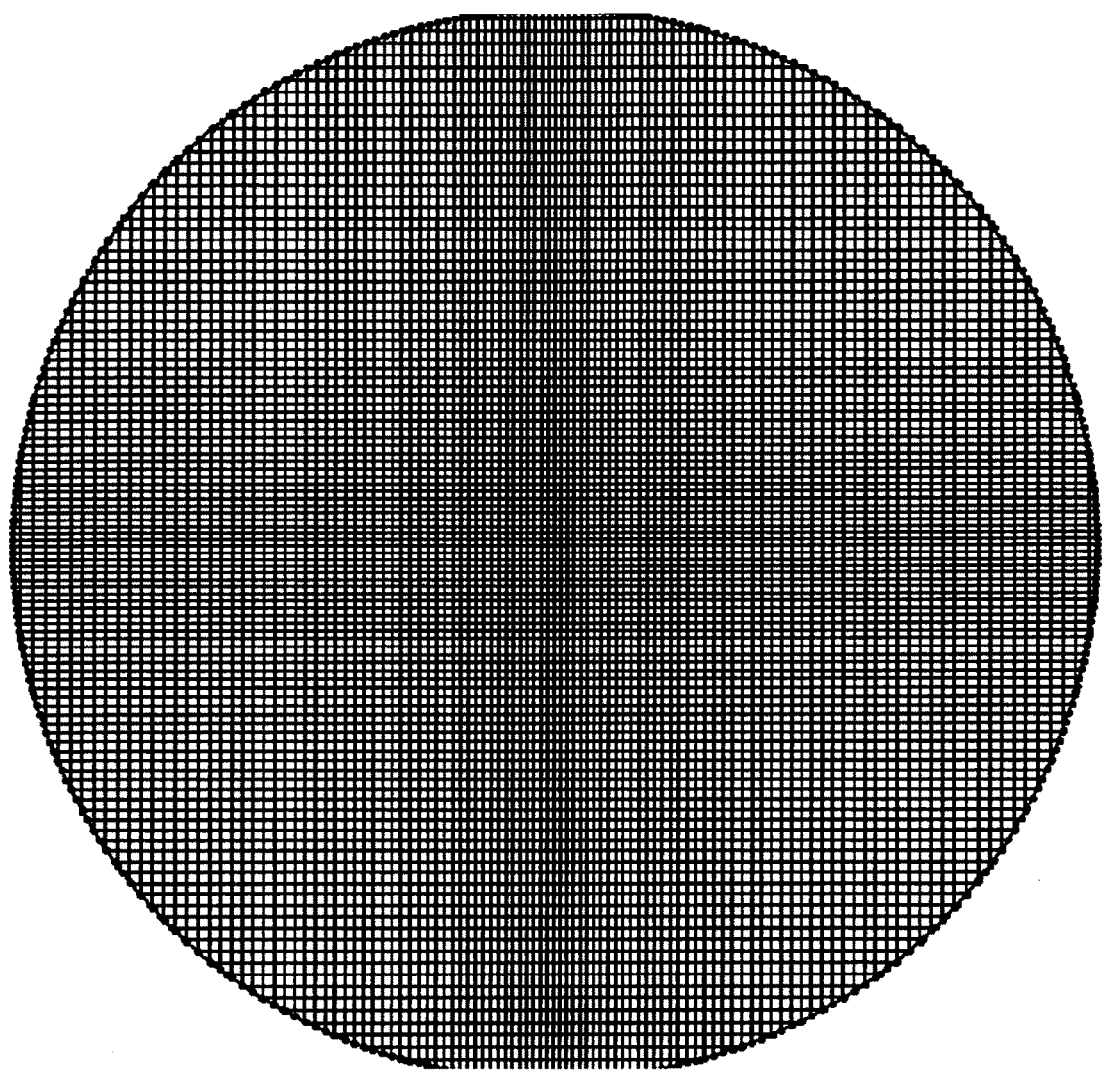
FIG. 32 is a schematic two-dimensional sketch of the grid in FIG. 31, according to an illustrative aspect of the invention.

Given the grid spacing terms recited above, a two-dimensional sketch was created showing the rectangular (non-warped) planar grid with each line dimensioned from the calculations in Table 1. The resulting sketch is shown in FIG. 32.

Figure 33:
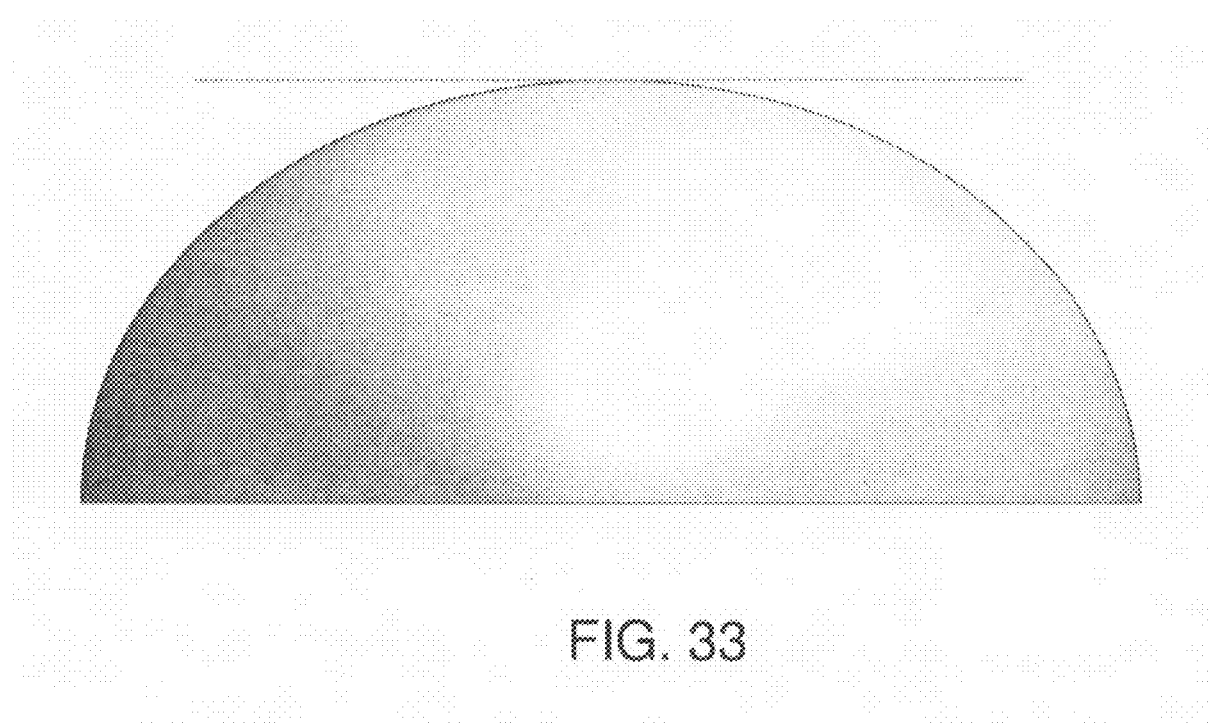
FIG. 33 is a side view of the grid sketch tangent to sphere surface, according to an illustrative aspect of the invention.
Figure 34:
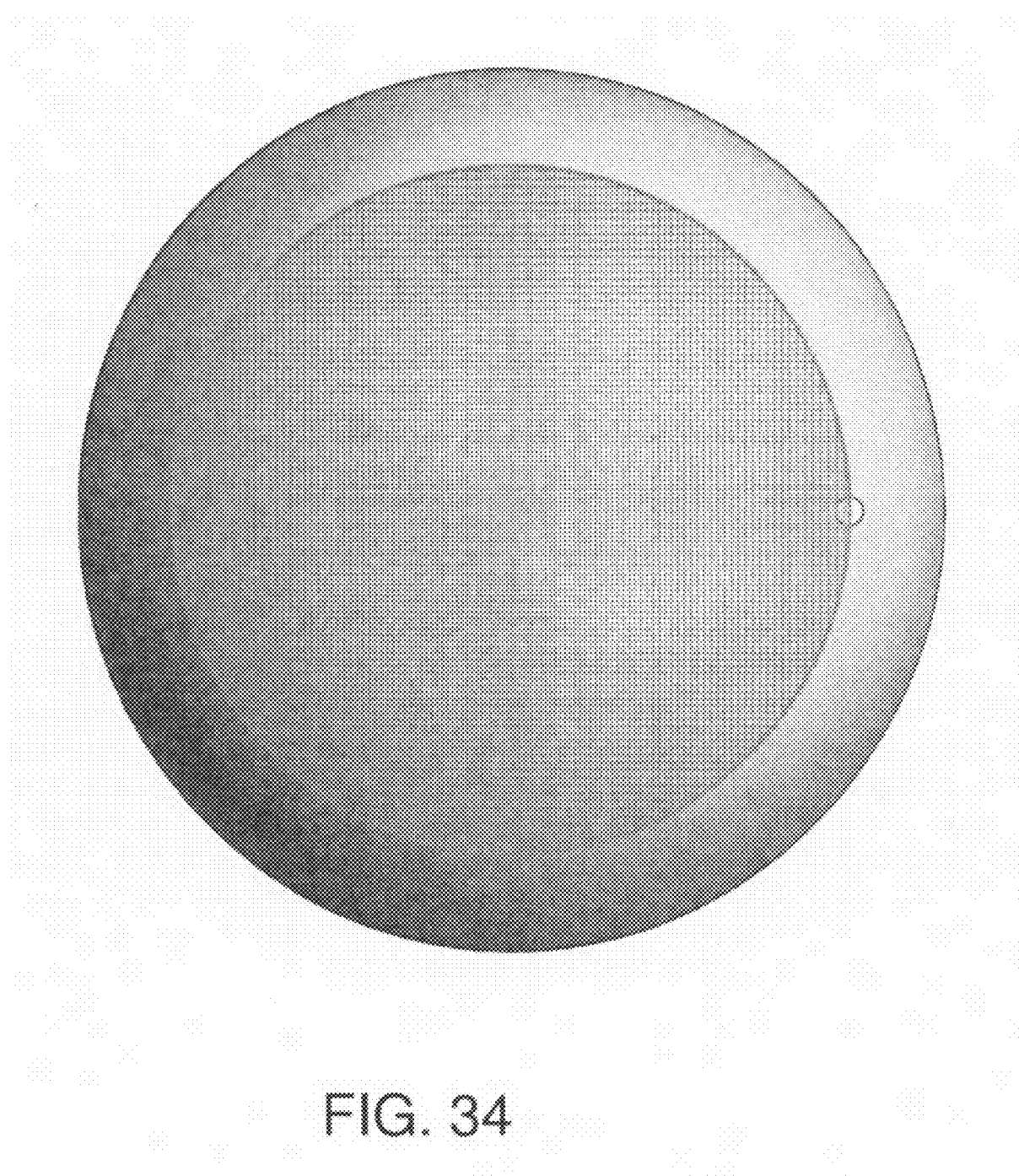
FIG. 34 is a top view of the grid sketch tangent to sphere surface, according to an illustrative aspect of the invention.
Figure 35:
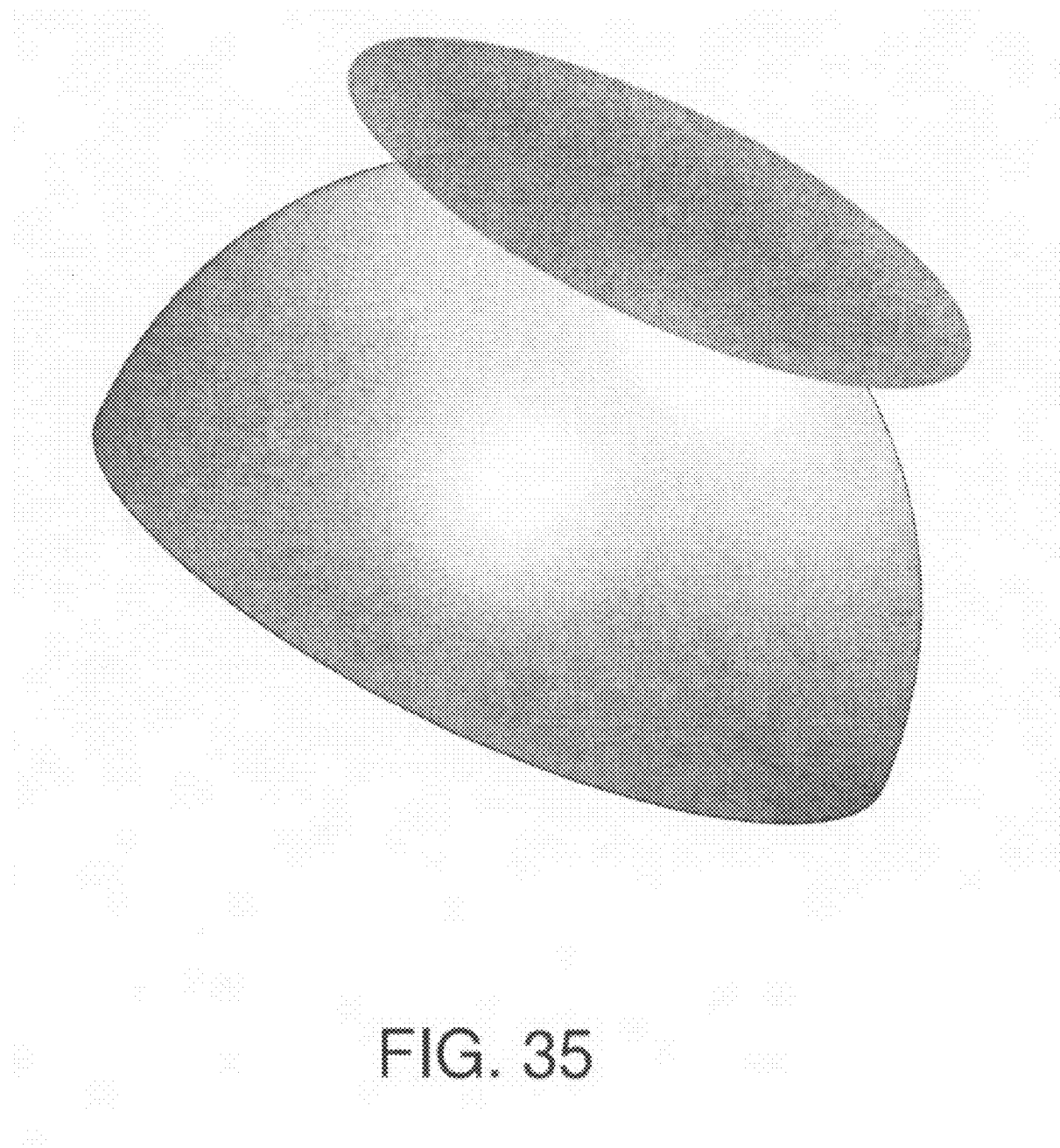
FIG. 35 is an isometric view of the grid sketch tangent to sphere surface, according to an illustrative aspect of the invention.

After the sketch was created, an 8.0 mm sphere was modeled and placed tangent to the 2-D grid sketch at the center of the grid sketch and the apex of the sphere. This placement is show in FIGS. 33, 34 and 35.

Figure 36:
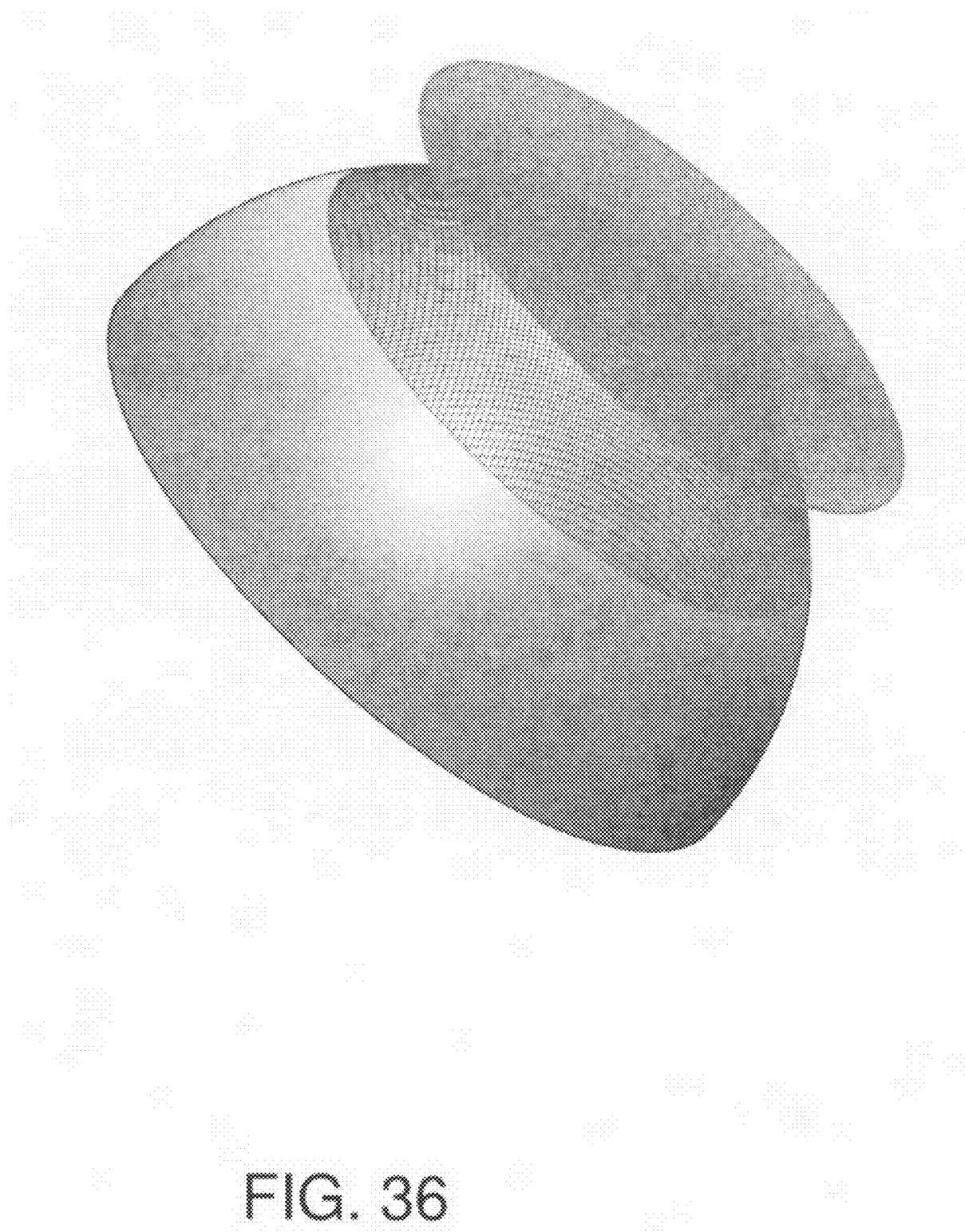
FIG. 36 is a 2-D grid sketch extruded onto a 3-D surface, according to an illustrative aspect of the invention.

After placement of the grid sketch in relation to the sphere surface, the grid sketch was extruded into a zero thickness surface of 8 mm diameter with the sphere surface apex at the grid origin as illustrated in FIG. 36.

Figure 37:
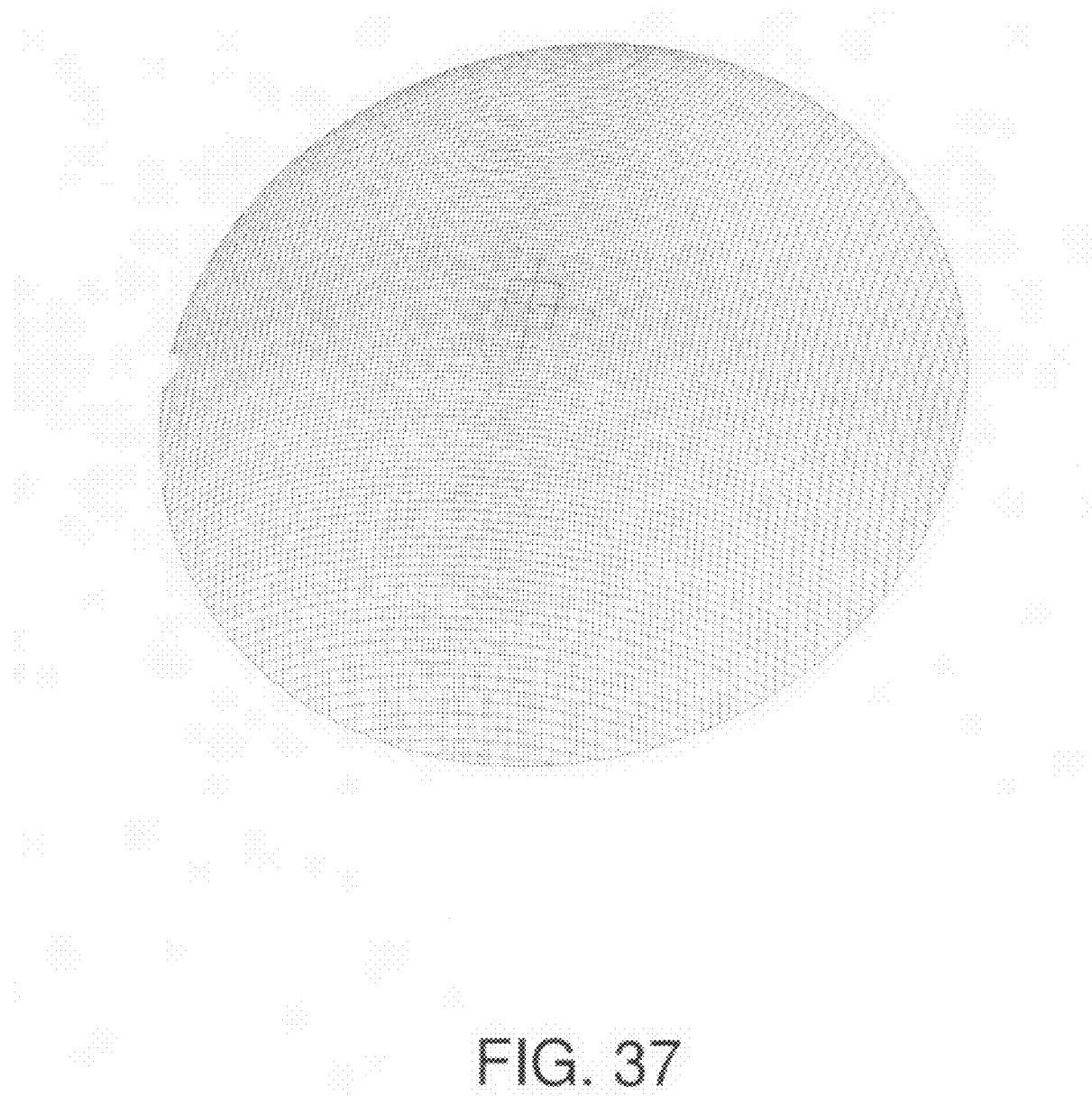
FIG. 37 is a 2-D grid sketch extruded onto a 3-D surface, with center crosshair and circular registration, according to an illustrative aspect of the invention.
Figure 38:
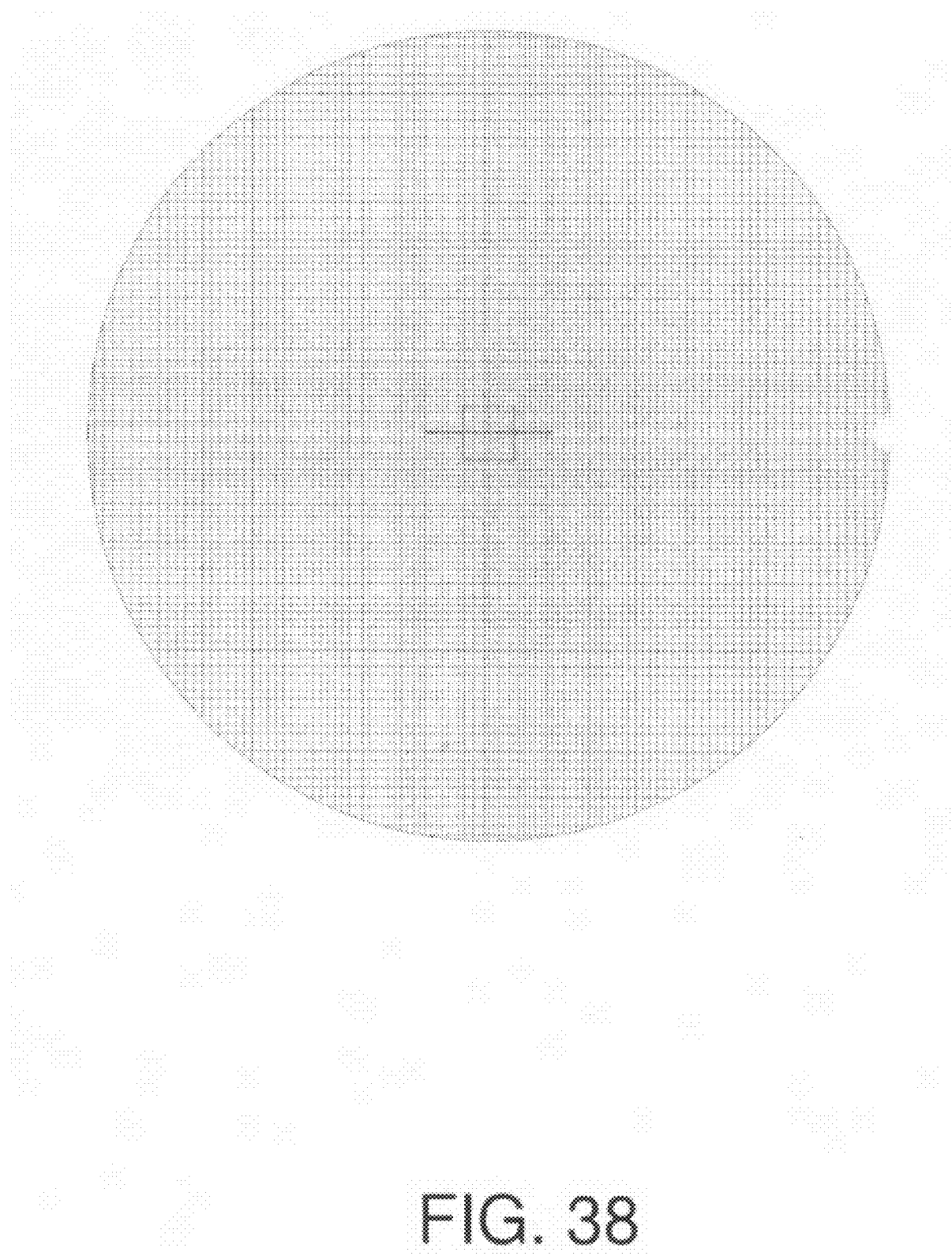
FIG. 38 is a 2-D grid sketch viewed along the normal of the grid surface, according to an illustrative aspect of the invention.
Figure 39:
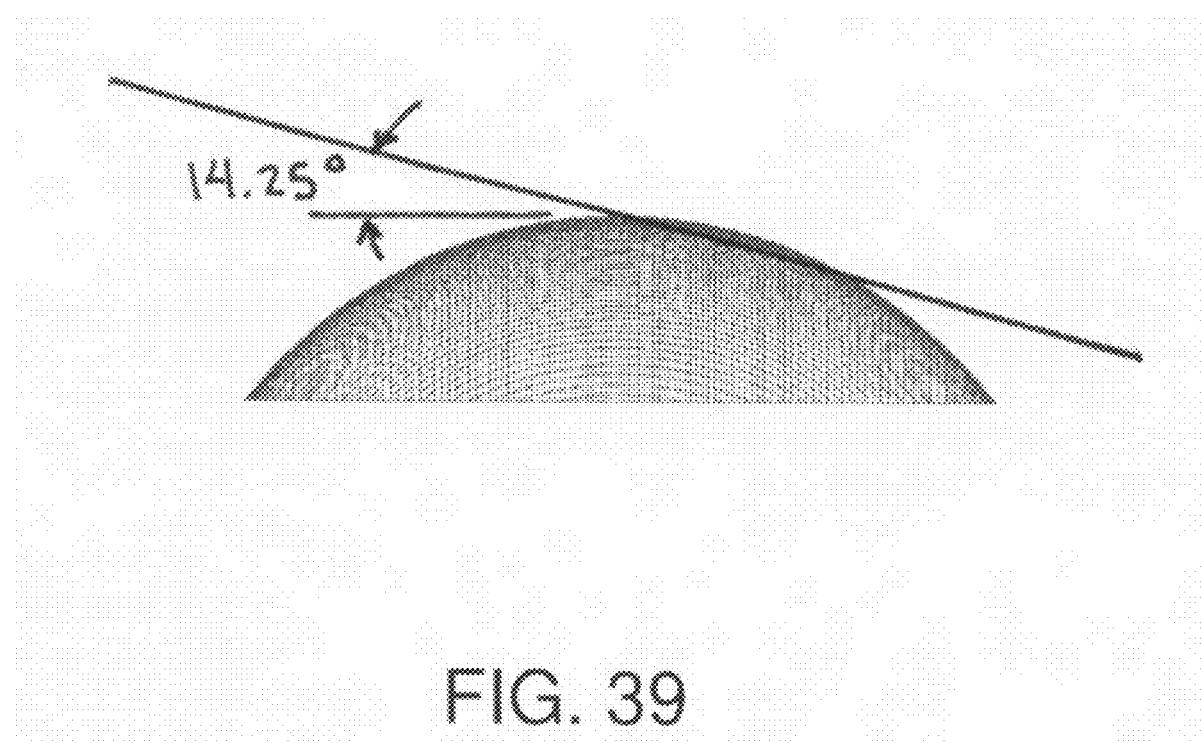
FIG. 39 shows a plane 14.25 degrees offset from a normal plane, according to an illustrative aspect of the invention.
Figure 40:
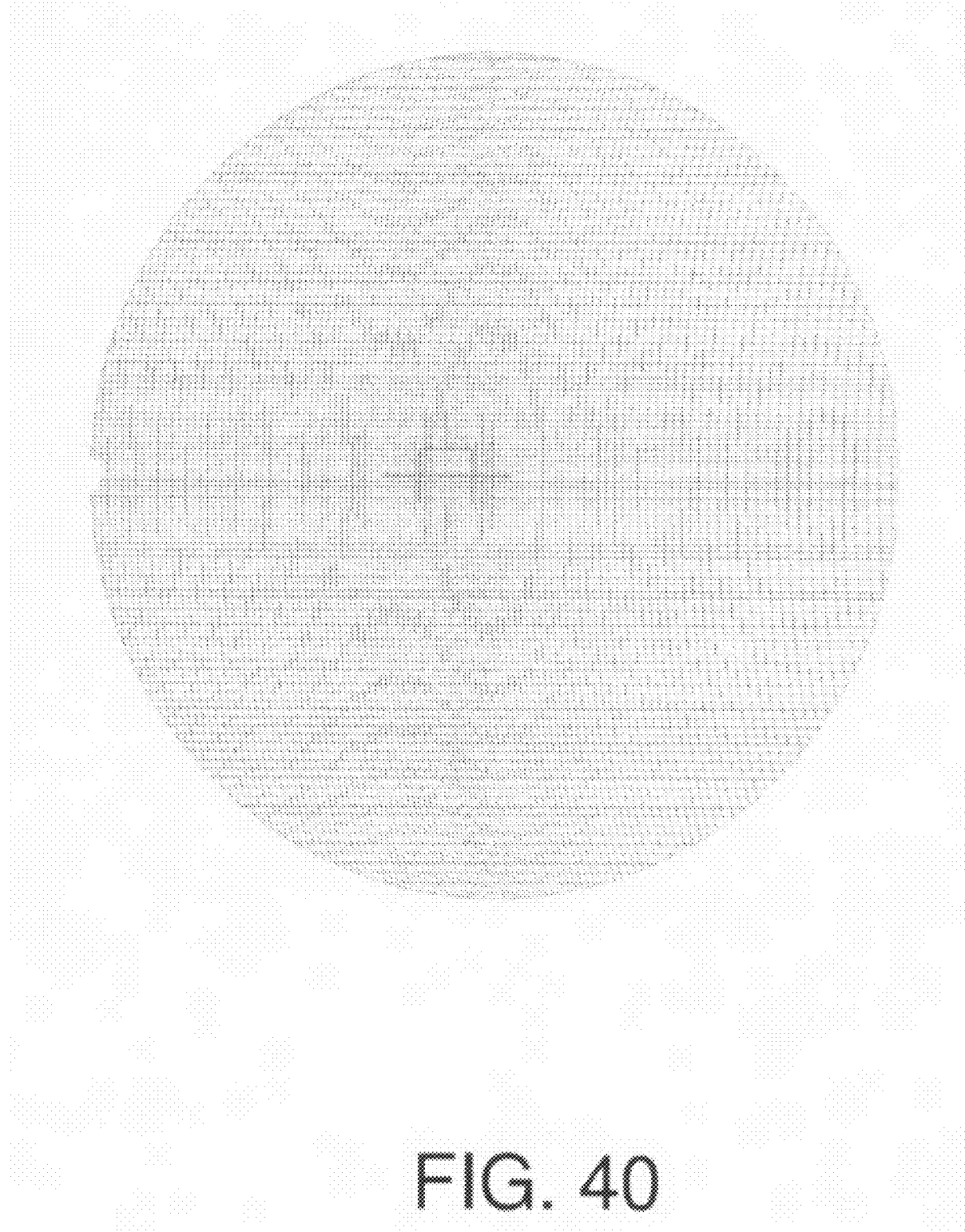
FIG. 40 shows a warped grid pattern as viewed from 14.25 degrees from a normal plane, according to an illustrative aspect of the invention.

A center bold crosshair and circular registration cutout were then added. The registration cut allows for physical placement of the grid reticle within the optical system. The resulting 3-D surface is illustrated in FIG. 37. When this 3-D surface is viewed from above and normal to the surface, the grid appears rectangular as illustrated in FIG. 38. However, when this grid is viewed from an angle offset from a normal plane, the warped grid patter appears, in this example 15.25 degrees. This angle may be altered as necessary to accommodate differing optical layouts. A normal plane is a plane lying tangent to the surface along a perpendicular normal. This plane is illustrated in FIG. 39 and the resulting view from this plane is illustrated in FIG. 40.

Figure 41:
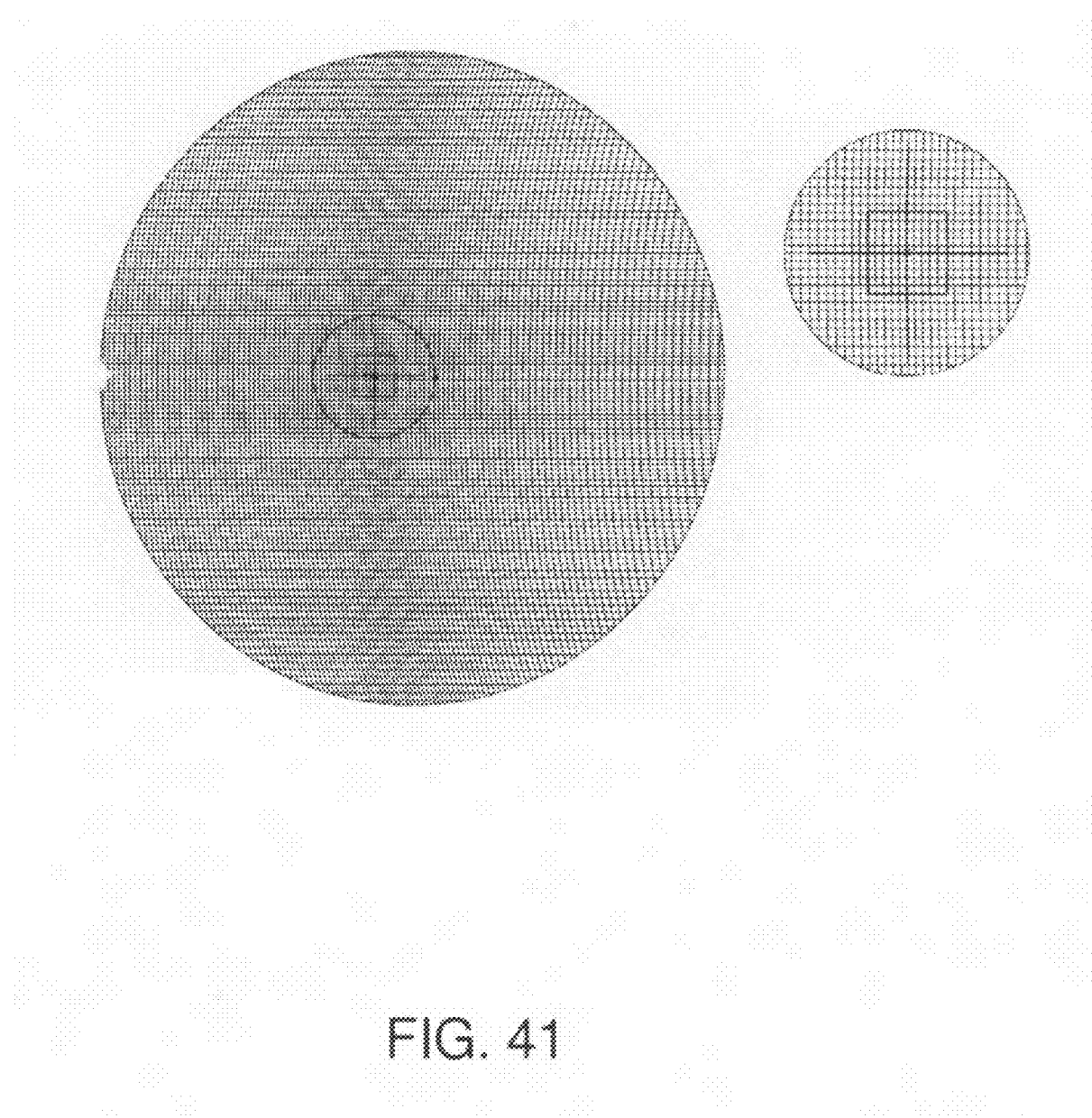
FIG. 41 shows a drawing used to fabricate the warped grid reticle, according to an illustrative aspect of the invention.

When plotted from the viewing angle described above, the drawing of the warped grid is created. This plot can then be used to fabricate the grid reticle. FIG. 41 shows the resulting plot.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed. No language in the specification should be construed as indicating any non-claimed element as essential to the practice of the invention.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

We claim:

1. A device for determining a dynamic deformation characteristic of an object having a deformable surface, comprising:
    a topographer component that is capable of making a spatially resolved measurement of a selected topographical characteristic of the object both before and during a deformation time interval;
    a non-contact object surface-deformer component disposed along a first, directionally-independent device axis, which is capable of providing a non-contact deformation force during the deformation time interval; and
    a controller/processor component connected to the topographer component and the non-contact object surface-deformer component,
    wherein the topographer component and the non-contact object surface-deformer component are operationally integrated so as to provide an object surface deformation force via the non-contact object surface-deformer component during the deformation time interval and to make the spatially resolved measurement of the selected topographical characteristic of the object via the topographer component both before and during the deformation time interval over which the object surface is deformed.

2. The device of claim 1, wherein the selected topographical characteristic is selected from a list consisting of surface displacement, surface curvature, surface elevation, surface indentation, surface deformation symmetry, surface deformation shape, and surface deformation area.

3. The device of claim 1, wherein the topographer component further comprises an optical system, including a camera assembly disposed along a second, directionally-independent device axis, that can capture an image of the selected topographical characteristic of the object and a grid projection assembly disposed along a third, directionally-independent device axis that can project a grid image onto the object surface.

4. The device of claim 3, wherein the optical system comprises a controllable, multi-wavelength, variable intensity LED illumination system.

5. The device of claim 3, wherein the grid projection assembly includes a grid reticle and an illumination system having a wavelength-controllable and an intensity-controllable light source.

6. The device of claim 5, wherein the grid reticle comprises a warped grid.

7. The device of claim 5, wherein a warped grid image projected onto the corneal surface has a constant line spacing in at least one of a horizontal and a vertical direction.

8. The device of claim 5, wherein a warped grid image projected onto the corneal surface has a variable line spacing in at least one of a horizontal and a vertical direction.

9. The device of claim 1, wherein the first device axis is a central axis of the device along which the object will be located.

10. The device of claim 1, wherein the dynamic deformation characteristic is selected from a group consisting of stiffness, strain, elasticity, viscosity, and viscoelasticity.

11. The device of claim 1, wherein the non-contact deformation force is a non-constant force.

12. A device for determining dynamic, in-vivo, elastic and viscoelastic properties of a cornea of an eye, comprising:
    a topographer component that is capable of making a spatially resolved measurement of a selected topographical characteristic of the in-vivo cornea both before and during a deformation time interval;
    a non-contact corneal surface-deformer component disposed along a first, directionally-independent device axis that can deliver a controlled in vivo corneal surface deformation during the deformation time interval; and
    a controller/processor component connected to the topographer component and the non-contact surface-deformer component,
    wherein the topographer component and the non-contact surface-deformer component are operationally integrated so as to provide the in-vivo corneal surface deformation via the non-contact object surface-deformer component during the deformation time interval and make the spatially resolved measurement of the selected topographical characteristic of the in-vivo corneal surface via the topographer component both before and during the deformation time interval over which the object surface is deformed,
    further wherein the determined dynamic, in-vivo, elastic and viscoelastic properties comprises viscoelasticity of the cornea.

13. The device of claim 12, wherein the selected topographical characteristic is selected from a list consisting of corneal surface displacement, corneal surface curvature, corneal surface elevation, corneal surface indentation, corneal surface deformation symmetry, corneal surface deformation shape, and corneal surface deformation area.

14. The device of claim 12, wherein the topographer component further comprises an optical system, including a camera assembly disposed along a second, directionally-independent device axis, that can capture at least a single pre-deformation corneal image and at least a single intra-deformation corneal image, and a grid projection assembly disposed along a third, directionally-independent device axis, that can project a grid image onto the corneal surface.

15. The device of claim 14, wherein the grid projection assembly includes a grid reticle and an illumination system having a wavelength-controllable and an intensity-controllable light source.

16. The device of claim 15, wherein the grid reticle comprises a warped grid.

17. The device of claim 16, wherein a grid image projected onto the in-vivo corneal surface has a constant line spacing in at least one of a horizontal and a vertical direction.

18. The device of claim 16, wherein a grid image projected onto the in-vivo corneal surface has a variable line spacing in at least one of a horizontal and a vertical direction.

19. The device of claim 12, wherein the first device axis is a central axis of the device along which the in-vivo cornea will be located.

20. The device of claim 12, wherein the topographer component is a rastersterographer.

21. The device of claim 12, wherein the controlled in-vivo corneal surface deformation force is a calibrated air puff that provides a distributed force over the surface of the cornea.

22. The device of claim 12, further wherein the dynamic, in-vivo, elastic and viscoelastic properties of the in-vivo cornea are selected from a group consisting of stiffness, strain, elasticity, and viscosity.

23. The device of claim 12, wherein the deformation time interval has a duration of less than 50 milliseconds.

24. The device of claim 12, wherein the non-contact deformation force is a non-constant force.

25. A method for determining quantitative elastic and viscoelastic properties of an in-vivo cornea of an eye, comprising:
obtaining at least only a single measurement image of a selected topographical characteristic of the in-vivo cornea in an undeformed state;
deforming the in-vivo cornea with a known amount of a non-contact force applied over at least a portion of a deformation time interval;
obtaining at least only a single measurement image of the selected topographical characteristic of the in-vivo cornea in a deformed state being due to the known amount of the non-contact force applied during at least the portion of the deformation time interval;
determining a difference between the measured pre- and intra-deformation topographical characteristics of the in-vivo cornea at least only a single spatial location on the cornea; and
deriving a biomechanical and/or a biodynamic measurement using this measured data, wherein the biomechanical and/or biodynamic measurement of the in-vivo cornea is selected from a group consisting of stiffness, strain, elasticity, viscosity, and viscoelasticity.

26. The method of claim 25, further comprising obtaining a plurality of topographical characteristic measurement images of the in-vivo cornea in the deformed state during the deformation interval.

27. The method of claim 26, further comprising determining a displacement of the in-vivo cornea surface between the undeformed state and the deformed state at least two spatially-resolved locations on the in-vivo cornea during the deformation interval.

28. The method of claim 25, wherein the steps of obtaining the measurement images of the selected topographical characteristics of the in-vivo cornea in the undeformed state and the deformed state comprises projecting a warped grid pattern image onto the in-vivo corneal surface.

29. The method of claim 25, further comprising:
identifying horizontal and vertical lines of a grid image projected onto the corneal surface;
identifying a plurality of grid nodes;
determining the x and y location of each grid node; and
determining a surface elevation value at least one spatial location relative to an instrument axis.

30. The method of claim 29, further comprising determining at least one of a stress value and a strain value at the at least one spatial location.

31. The method of claim 25, further comprising measuring in-vivo corneal stiffness, k, at least two different spatial locations, where $k=P/\delta$, where P is the applied non-contact force and $\delta$ is the resulting displacement at each spatial location, further wherein $\delta$ is provided via measurements of $\delta_{Pre-def}$ and $\delta_{During-def}$.

32. The method of claim 31, further comprising measuring in-vivo corneal stiffness at a plurality of different spatial locations over the entire in-vivo corneal-scleral region.

33. The method of claim 25, wherein the steps of deforming the in-vivo cornea with a known amount of a non-contact force applied over at least a portion of a deformation time interval, and obtaining at least only a single measurement image of the selected topographical characteristic of the in-vivo cornea in a deformed state being due to the known amount of the non-contact force applied during at least the portion of the deformation time interval are performed over the deformation time interval having a duration of less than 50 milliseconds.

34. The method of claim 25, wherein the step of deforming the in-vivo cornea with a known amount of a non-contact force further comprises applying a non-constant force.

* * * * *